(12) United States Patent  
Shimizu et al.

(10) Patent No.: US 10,011,568 B2  
(45) Date of Patent: Jul. 3, 2018

(54) CYCLOHEXYL PYRIDINE DERIVATIVE

(71) Applicant: KISSEI PHARMACEUTICAL CO., LTD., Matsumoto, Nagano (JP)

(72) Inventors: Kazuo Shimizu, Azumino (JP); Kohsuke Ohno, Azumino (JP); Takashi Miyagi, Azumino (JP); Yasunori Ueno, Azumino (JP); Hikaru Suzuki, Azumino (JP)

(73) Assignee: KISSEI PHARMACEUTICAL CO., LTD., Matsumoto, Nagano (JP)

( * ) Notice: Subject to any disclaimer, the term of this patent is extended or adjusted under 35 U.S.C. 154(b) by 0 days.

(21) Appl. No.: 15/630,238

(22) Filed: Jun. 22, 2017

(65) Prior Publication Data

US 2017/0298024 A1  Oct. 19, 2017

Related U.S. Application Data

(62) Division of application No. 15/308,996, filed as application No. PCT/JP2015/063154 on May 7, 2015, now Pat. No. 9,708,266.

(30) Foreign Application Priority Data

May 7, 2014  (JP) ................. 2014-095776

(51) Int. Cl.
   C07D 213/75   (2006.01)
   C07D 213/84   (2006.01)

(52) U.S. Cl.
   CPC ......... *C07D 213/75* (2013.01); *C07D 213/84* (2013.01)

(58) Field of Classification Search
   CPC ... C07D 213/75; C07D 213/94; C07D 213/84
   See application file for complete search history.

(56) References Cited

U.S. PATENT DOCUMENTS

| | | | |
|---|---|---|---|
| 6,225,316 B1 | 5/2001 | Bös et al. |
| 6,297,375 B1 | 10/2001 | Bös et al. |
| 6,479,483 B2 | 11/2002 | Bös et al. |
| 6,576,762 B2 | 6/2003 | Hoffmann et al. |
| 6,593,472 B2 | 7/2003 | Hoffmann et al. |
| 6,770,637 B2 | 8/2004 | Godel et al. |
| 6,849,624 B2 | 2/2005 | Ballard et al. |
| 7,211,579 B2 | 5/2007 | Funk et al. |
| 7,683,056 B2 | 3/2010 | Alvaro et al. |
| 7,939,533 B2 | 5/2011 | Hoffmann et al. |
| 8,344,005 B2 | 1/2013 | Alvaro et al. |
| 8,426,450 B1 | 4/2013 | Fadini et al. |
| 2003/0004157 A1 | 1/2003 | Buser et al. |
| 2003/0083345 A1 | 5/2003 | Hoffmann et al. |
| 2006/0030600 A1 | 2/2006 | Schnider |
| 2007/0071813 A1 | 3/2007 | Ahmed et al. |
| 2010/0197652 A1 | 8/2010 | Bergman et al. |
| 2011/0060015 A1 | 3/2011 | Alvaro et al. |
| 2016/0289206 A1 | 10/2016 | Shimizu et al. |

FOREIGN PATENT DOCUMENTS

| | | |
|---|---|---|
| EP | 1 103 545 A1 | 5/2001 |
| JP | 2000-247957 A | 9/2000 |
| JP | 2010-535769 A | 11/2010 |
| JP | 2011-520834 A | 7/2011 |
| WO | 2011/054773 A1 | 5/2011 |
| WO | 2015/068744 A1 | 5/2015 |

OTHER PUBLICATIONS

Bissantz et al., "Identification of a Crucial Amino Acid in the Helix Position 6.51 of Human Tachykinin Neurokinin 1 and 3 Receptors Contributing to the Insurmountable Mode of Antagonism by Dual NK1/NK3 Antagonists", American chemical Society, J. Med. Chem., vol. 55, pp. 5061-5076, 2012.

International Search Report dated Aug. 4, 2015, issued in counterpart International Application No. PCT/JP2015/063154 (2 pages; in English).

*Primary Examiner* — Timothy R Rozof  
(74) *Attorney, Agent, or Firm* — Westerman, Hattori, Daniels & Adrian, LLP

(57) ABSTRACT

A problem of the present invention is to provide a new compound which has $NK_1$ receptor antagonist activity, whose CYP3A4 inhibitory activity is reduced compared to aprepitant, and which are useful for the prevention or treatment of cancer-chemotherapy-induced nausea and vomiting. That is, the present invention relates to cyclohexyl pyridine derivatives represented by the following formula (I) or a pharmaceutically acceptable salt thereof, wherein, ring A is 4-fluoro-2-methylphenyl or the like; X is a hydrogen atom or the like; $R^1$ is carboxymethyl or the like; $R^2$ is alkyl or the like; Y is 0-2 or the like; U is $-N(CH_3)COC(CH_3)_2$-3,5-bistrifluoromethylphenyl or the like.

Formula (I):

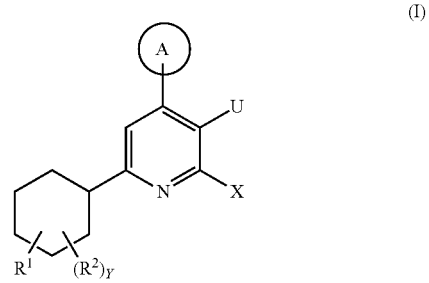

13 Claims, 1 Drawing Sheet

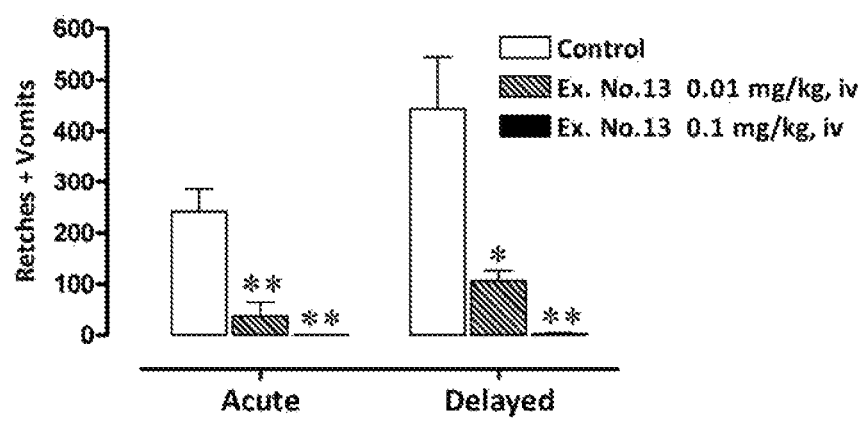

CYCLOHEXYL PYRIDINE DERIVATIVE

CROSS REFERENCE

This Application is a divisional of U.S. application Ser. No. 15/308,996 filed on Nov. 4, 2016, which is a U.S. national stage of International Application No. PCT/JP2015/063154 filed on May 7, 2015, each of which claims benefit of Japanese Patent Application No. 2014-095776, filed on May 7, 2014, the entire contents of each of the foregoing are herein incorporated by reference.

TECHNICAL FIELD

The present invention relates to cyclohexyl pyridine derivatives useful as medicaments.

More particularly, the present invention relates to cyclohexyl pyridine derivatives or pharmaceutically acceptable salts thereof which have substance P/neurokinin 1 ($NK_1$) receptor antagonist activity, and which are useful as agents for the prevention or treatment of cancer-chemotherapy-induced nausea and vomiting (CINV) and so on.

BACKGROUND ART

CINV occurs when the vomiting center located in the lateral reticular formation of the medulla oblongata receives a stimulus. The area postrema and the solitary nucleus of the medulla oblongata contain $NK_1$ receptors, and the $NK_1$ receptors are believed to be closely involved in vomiting.

Administration of an antineoplastic agent facilitates the serotonin secretion from the enterochromaffin (EC) cells in the digestive tract, and serotonin directly stimulates the vomiting center through 5-hydroxytryptamine, ($5\text{-}HT_3$) receptors in the digestive tract. Also, when serotonin stimulates the vomiting center through the chemoreceptor trigger zone (CTZ) located in the area postrema of the fourth ventricle, nausea and vomiting occur. Substance P, like serotonin, is found in the EC cells in the digestive tract, and its secretion is promoted by administration of an amineoplastic agent. Recently, it has been revealed that substance P induces vomiting through the $NK_1$ receptors in the CTZ or by binding to the $NK_1$ receptors in the central nervous system, and therefore $NK_1$ receptors have been attracting attention as the target for developing antiemetic agents (Non-patent literature 1).

Aprepitant is the first selective $NK_1$ receptor antagonist in the world which was approved as a preventive agent for nausea and vomiting associated with administration of antineoplastic agents. Regarding the mechanism of action of aprepitant, it is believed that aprepitant selectively inhibits the binding of substance P and the $NK_1$ receptors in the central nervous system, which is one of the pathways that induce CINV, and thus prevents CINV. Aprepitant has been launched as a preventive agent for CINV (Non-patent literature 2).

It is known that aprepitant is metabolized by cytochrome P450 (CYP) 3A4. Also, aprepitant is known to have a dose-dependent inhibitory effect on CYP3A4, a CYP3A4-inducing effect and a CYP2C9-inducing effect. Accordingly, aprepitant may cause the drug-drug interactions with drugs that inhibit or induce CYP3A4 or with drugs that are metabolized by CYP3A4 or CYP2C9. For example, it is reported that the inhibitory effect of aprepitant on CYP3A4 sometimes inhibits the metabolism of dexamethasone and that the dose should be thus adjusted when dexamethasone is combined with aprepitant (Non-patent literature 3).

Therefore, when aprepitant is used, sufficient care should be directed to the drug-drug interactions based on the inhibitory effect of aprepitant on CYP3A4.

For the above reasons, a novel $NK_1$ receptor antagonist with fewer drug-drug interactions is required in the prevention or treatment of CINV.

Compounds with an $NK_1$ receptor antagonist activity such as casopitant, netupitant, exlopitant, rolapitant, vestipitant, vofopitant and so on, are known.

However, casopitant is reported to have an inhibitory effect on CYP3A4 and cause the drug-drug interactions due to the effect (Non-patent literature 4). Clinical trials on casopitant, as a preventive agent for cancer-chemotherapy-induced nausea and vomiting, had been conducted in the U.S. and Europe: however, its development was discontinued after the application. Netupitant is currently under development as a preventive agent for cancer-chemotherapy-induced nausea and vomiting; however, netupitant is reported to have an inhibitory effect on CYP3A4 and cause the drug-drug interactions due to the effect (Non-patent literature 5). Clinical trials on ezlopitant, as a preventive agent for cancer-chemotherapy-induced nausea and vomiting, had been conducted in the U.S.; however, its development was discontinued. Clinical trials on vofopitant, as a preventive agent for cancer-chemotherapy-induced nausea and vomiting, had been conducted in Europe: however, its development was discontinued.

Many of the above compounds resulted in the discontinuance. All the above compounds have not yet on the market.

Pyridine derivatives claiming to be having $NK_1$ receptor antagonist activity are described in Patent literature 1 to 16. And, prodrugs of pyridine derivatives are described in Patent literature 17 and 18.

However, cyclohexyl pyridine derivatives of the present invention are not described in the above literatures.

CITATION LIST

Patent Literature

Patent literature 1: U.S. Pat. No. 6,479,483
Patent literature 2: U.S. Pat. No. 6,770,637
Patent literature 3: U.S. Pat. No. 7,939,533
Patent literature 4: European Patent No. 1,103,545
Patent literature 5: U.S. Pat. No. 7,211,579
Patent literature 6: U.S. Patent Publication No. 2006/0030600
Patent literature 7: U.S. Pat. No. 6,576,762
Patent literature 8: U.S. Pat. No. 6,225,316
Patent literature 9: U.S. Pat. No. 7,683,056
Patent literature 10: U.S. Pat. No. 8,344,005
Patent literature 11: International publication No. WO2011/054773
Patent literature 12: U.S. Patent Publication No. 2007/0071813
Patent literature 13: U.S. Patent Publication No. 2003/0083345
Patent literature 14: U.S. Patent Publication No. 2003/0004157
Patent literature 15: U.S. Pat. No. 6,849,624
Patent literature 16: U.S. Pat. No. 6,297,375
Patent literature 17: U.S. Pat. No. 6,593,472
Patent literature 18: U.S. Pat. No. 8,426,450

Non-Patent Literature

Non-patent literature 1: P. J. Hesketh et al., European Journal of Cancer, 2003, Vol. 39. pp. 1074-1080

Non-patent literature 2: Toni M. Dando et al., Drugs, 2004, Vol. 64, No. 1, pp. 777-794

Non-patent literature 3: Jacqueline B. McCrea et al., CLINICAL PHARMACOLOGY & THERAPEUTICS, 2003, Vol. 74, No. 1, pp. 17-24

Non-patent literature 4: Stefano Zamuner et al., British Journal of Clinical Pharmacology, 2010, Vol. 70, No. 4, pp. 537-546

Non-patent literature 5: Corinna Lanzarotti et al., Support Care Cancer, 2013, Vol. 21, No. 10, pp. 2783-2791

SUMMARY OF THE INVENTION

Problem to be Solved by the Invention

A problem of the present invention is to provide a new compound which has $NK_1$ receptor antagonist activity, whose CYP3A4 inhibitory activity is reduced compared to aprepitant, and which are useful for the prevention or treatment of cancer-chemotherapy-induced nausea and vomiting. A problem of the present invention is preferably to provide the above compound whose central transportation property and long-acting medicinal effect is excellent.

Means for Solving the Problem

The present invention relates to a compound represented by the following formula (I) or a pharmaceutically acceptable salt thereof.

That is, the present invention relates to the following [1] to [12] and the like.

[1] A compound represented by the formula (I):

[Chem. 1]

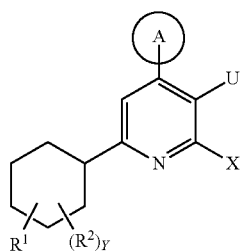

(I)

wherein
ring A is a group represented by the following formula:

[Chem. 2]

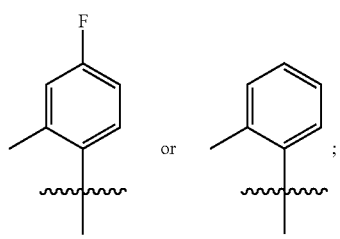

X is a hydrogen atom, cyano, halogen, $C_{1-6}$ alkyl or hydroxymethyl;

$R^1$ is a group represented by the following formula:

[Chem. 3]

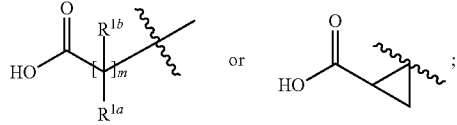

wherein
$R^{1a}$ and $R^{1b}$ are each independently any one of a hydrogen atom, a fluorine atom or $C_{1-6}$ alkyl;
m is 0, 1 or 2;
when m is 2, these $R^{1a}$ and $R^{1b}$ are optionally different from each other;
$R^2$ is $C_{1-6}$ alkyl, a hydroxy group or $C_{1-6}$ alkoxy;
U is a group represented by the following formula:

[Chem. 4]

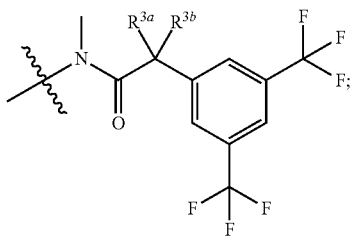

wherein
$R^{3a}$ and $R^{3b}$ are each independently a hydrogen atom, $C_{1-6}$alkyl, hydroxy $C_{1-6}$alkyl or $C_{1-6}$alkoxy$C_{1-6}$alkyl;
Y is 0, 1 or 2;
when Y is 2, two $R^2$ are optionally different from each other;
or a pharmaceutically acceptable salt thereof.

[2] The compound represented by the formula (Ia) according to the above [1];

[Chem. 5]

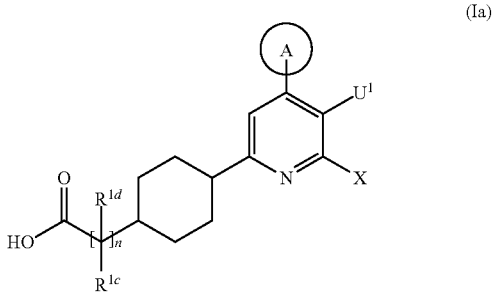

(Ia)

wherein
ring A and X have the same meaning as described in the above [1];
$R^{1c}$ and $R^{1d}$ are each independently a hydrogen atom or methyl;

$U^1$ is a group represented by the following formula:

[Chem. 6]

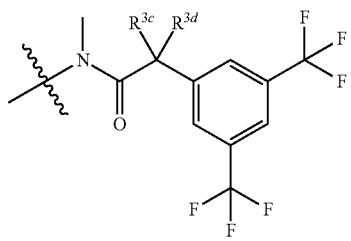

in which $R^{3c}$ and $R^{3d}$ and are each independently a hydrogen atom, methyl or hydroxymethyl;

n is 0, 1 or 2;

when n is 2, these $R^{1c}$ and $R^{1d}$ are optionally different from each other;

or a pharmaceutically acceptable salt thereof.

[3] The compound represented by the formula (Ib) according to the above [2]:

[Chem. 7]

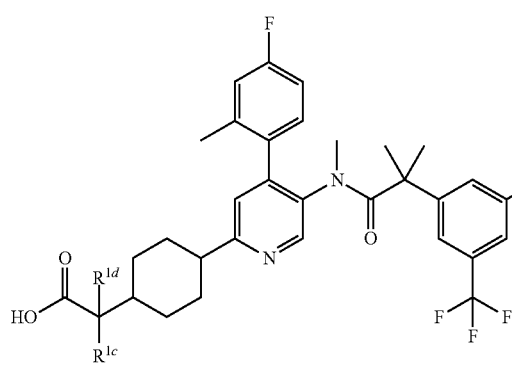

(Ib)

wherein $R^{1c}$ and $R^{1d}$ have the same meaning as described in the above [2];

or a pharmaceutically acceptable salt thereof.

[4] The compound represented by the following formula according to the above [1]:

[Chem. 8]

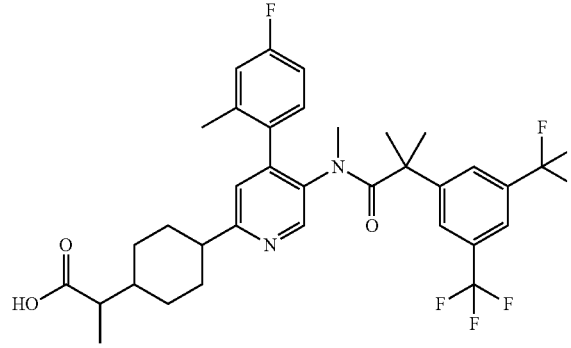

or a pharmaceutically acceptable salt thereof.

[5] The compound represented by the following formula according to the above [1];

[Chem. 9]

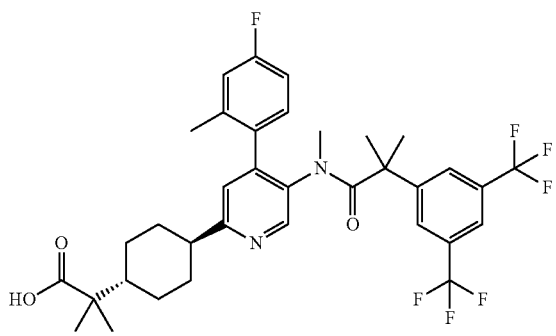

or a pharmaceutically acceptable salt thereof.

[6] The compound represented by the following formula according to the above [1]:

[Chem. 10]

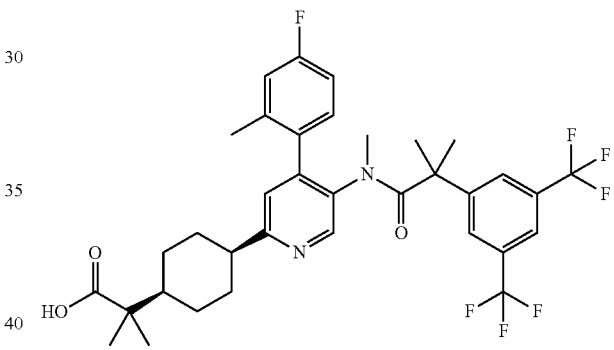

or a pharmaceutically acceptable salt thereof.

[7] The compound represented by the following formula according to the above [1]:

[Chem. 11]

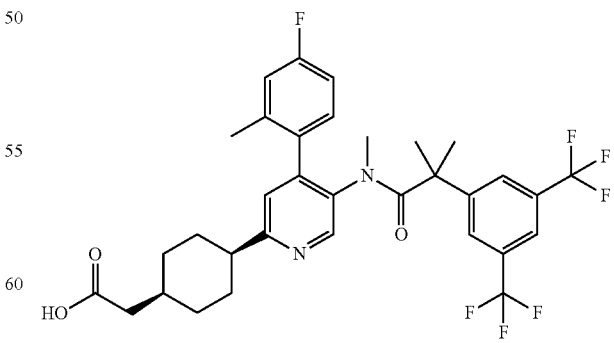

or a pharmaceutically acceptable salt thereof.

[8] The compound represented by the following formula according to the above [1]:

[Chem. 12]

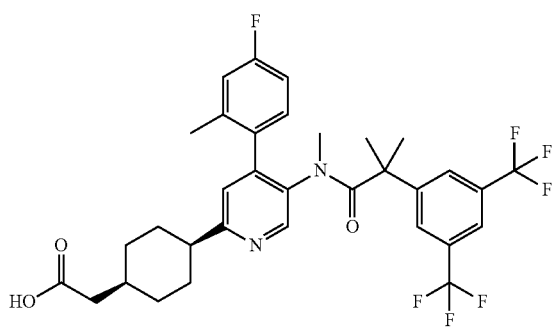

or a pharmaceutically acceptable salt thereof.

[9] The compound represented by the following formula according to the above [1]:

[Chem. 13]

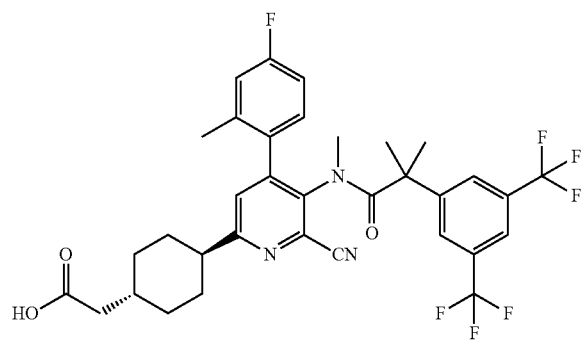

or a pharmaceutically acceptable salt thereof.

[10] The compound represented by the following formula according to the above [1]:

[Chem. 14]

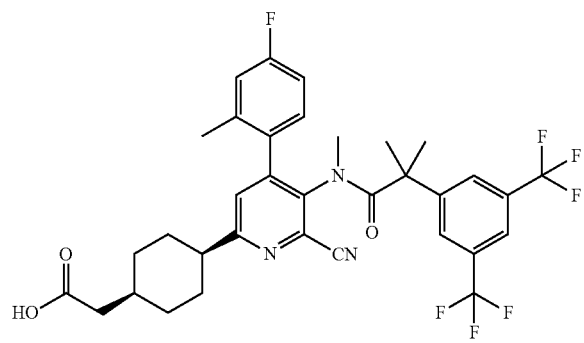

or a pharmaceutically acceptable salt thereof.

[11] A pharmaceutical composition comprising as an active ingredient a compound according to any one of the above [1] to [10], or a pharmaceutically acceptable salt thereof.

[12] The pharmaceutical composition according to the above [11], for use in the prevention of cancer-chemotherapy-induced nausea and vomiting.

Effect of the Invention

The compounds of the present invention have an excellent $NK_1$ receptor antagonist activity. And, CYP3A4 inhibitory activity of the compounds of the present invention is reduced compared to aprepitant. The preferable compounds of the present invention excel in central transportation property. The more preferable compounds of the present invention excel in central transportation property and long-acting medicinal effect.

Therefore, the compounds of the present invention or pharmaceutically acceptable salts thereof are useful as an agent for die prevention or treatment of cancer-chemotherapy-induced nausea and vomiting.

BRIEF DESCRIPTION OF THE DRAWINGS

FIG. 1 shows the effect on cisplatin-induced acute and delayed emetic response in test example 6. In the FIGURE, each bar chart shows a value of control group (Control), the group intravenously administered with 0.01 mg/kg of the compound of Example 13 (Ex. No 13, 0.01 mg/kg, iv) and the group intravenously administered with 0.1 mg/kg of the compound of Example 13 (Ex. No 13, 0.1 mg/kg, iv) in the acute phase, and a value of control group, the group intravenously administered with 0.01 mg/kg of the compound of Example 13 (Ex. No 13, 0.01 mg/kg, iv) and the group intravenously administered with 0.1 mg/kg of the compound of Example 13 (Ex. No 13, 0.1 mg/kg, iv) in the delayed phase from the left respectively. The vertical axes show the number of retching and vomiting (Retches+Vomits) (the mean+standard error of 3 examples of control group, the mean+standard error of 3 examples of the group intravenously administered with 0.01 mg/kg, and the mean+standard error of 3 examples of the group intravenously administered with 0.1 mg/kg).

MODE FOR CARRYING OUT THE INVENTION

Hereinafter, embodiments of the present invention will be described in further detail.

In the present invention, each term has the following meaning unless otherwise specified.

The term "$C_{1-6}$alkyl" means a straight-chained or a branched alkyl group having 1 to 6 carbon atoms, and for example, methyl, ethyl, propyl, isopropyl, butyl, isobutyl, sec-butyl, tert-butyl and the like can be illustrated.

The term "$C_{1-6}$alkoxy" means a straight-chained or a branched alkoxy group having 1 to 6 carbon atoms, and for example, methoxy, ethoxy, propoxy, isopropoxy and the like can be illustrated.

The term "hydroxyl $C_{1-6}$alkyl" means an $C_{1-6}$alkyl group substituted with a hydroxy group such as a hydroxymethyl group, a 1-hydroxyethyl group, a 1-hydroxy-1,1-dimethylmethyl group, a 2-hydroxyethyl group, a 2-hydroxy-2-methylpropyl group, a 3-hydroxypropyl group and the like.

The term "$C_{1-6}$alkoxy$C_{1-6}$alkyl" means the above $C_{1-6}$alkyl substituted by the above $C_{1-6}$alkoxy.

In the case where the compounds represented by the formula (I) of the present invention contain one or more asymmetric carbon atoms, all stereoisomers in the R- or S-configuration at each of asymmetric carbons and their mixtures are included in the present invention. In such cases, racemic compounds, racemic mixtures, individual enantiomers and mixtures of diastereomers are included in the scope of the present invention. In the case where the compounds represented by the formula (I) of the present invention have the cis-trans isomers, all cis-trans isomers are included in the present invention.

In the present invention, stereochemical determination can also be determined according to well-known methods in the art. For example, see also "Tokuron NMR rittai kagaku", Kodansha, 2012, p. 59.

A compound represented by the formula (I) of the present invention can also be converted into pharmaceutically acceptable salts thereof according to a general method. As such salts, acid additive salts and salts with a base can be illustrated.

As the acid additive salt, an acid additive salt with a mineral acid such as hydrochloric acid, hydrobromic acid, hydroiodic acid, sulfuric acid, nitric acid, phosphoric acid and the like, and an acid additive salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like can be illustrated.

As the salt with a base, a salt formed with inorganic base such as a lithium salt, a sodium salt, a potassium salt, a calcium salt, a magnesium salt and the like, and a salt formed with organic base such as N-methyl-D-glucamine, N,N'-dibenzylethylenediamine, triethylamine, piperidine, morpholine, pyrrolidine, arginine, lysine, choline and the like.

In the present invention, a pharmaceutically acceptable salt also includes a solvate thereof with a pharmaceutically acceptable solvent such as water, ethanol or the like.

In the compounds represented by the formula (I) of the present invention, the symbol $R^1$ and $R^2$ means a substituent of the cyclohexane ring.

In an embodiment of the compound represented by the formula (I) of the present invention, as cyclohexane ring having a substituent on the ring, a group represented by the following formula can be illustrated.

[Chem. 15]

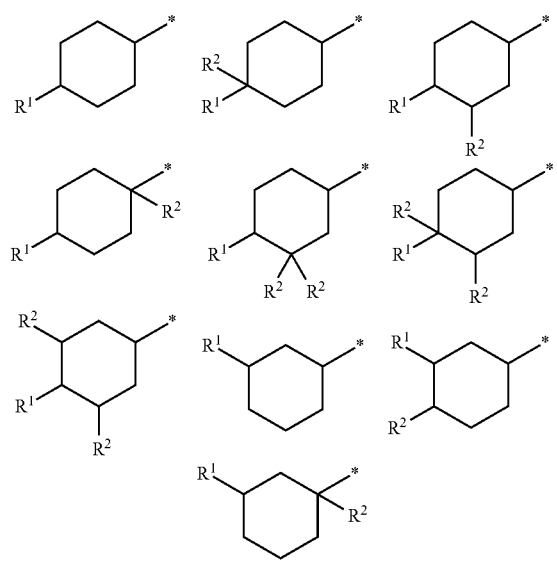

wherein, bonds with (*) are bonding site to the pyridine ring, and $R^1$ and $R^2$ have the same meaning as described in the above [1].

A compound represented by the formula (I) of the present invention can also be prepared, for example, by a method described below or a similar method thereto, or a method described in literatures or a similar method thereto.

Scheme 1

[Chem. 16]

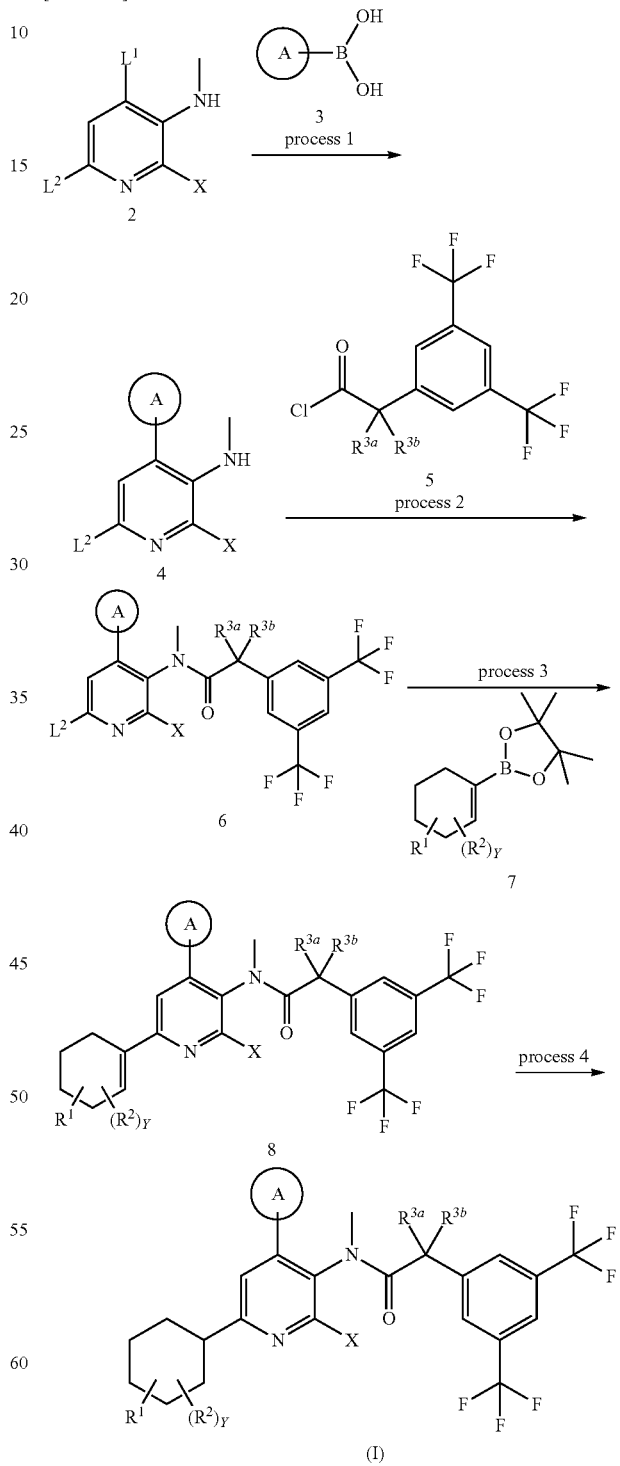

In the formula, $L^1$ and $L^2$ are each independently a leaving group such as a chlorine atom, a bromine atom, an iodine atom, a trifluoromethanesulfonyloxy group or the like and ring A, X, $R^1$, $R^2R^{3a}$, $R^{3b}$ and Y have the same meanings as defined above.

Process 1

Compound (4) can also be prepared by conducting coupling reaction of Compound (2) with Compound (3) in an inert solvent in the presence of a base and a palladium catalyst.

Process 2

Compound (6) can also be prepared by conducting condensation reaction of Compound (4) with Compound (5) in an inert solvent in the presence of a base.

Process 3

Compound (8) can also be prepared by conducting coupling reaction of Compound (6) with Compound (7) in an inert solvent in the presence of a base and a palladium catalyst.

As the inert solvent, for example, N,N-dimethylformamide, N-methylpyrrolidone, dimethylsulfoxide, diethyl ether, tetrahydrofuran, 1,4-dioxane, 1,2-dimethoxyethane, benzene, toluene, xylene, ethanol, water and a mixed solvent thereof can be illustrated. As the base, for example, potassium carbonate, sodium carbonate, cesium carbonate, sodium hydroxide, potassium hydroxide, lithium hydroxide, potassium fluoride, cesium fluoride, triethylamine, pyridine, N,N-diisopropylethylamine, 2,6-lutidine, and 1,8-diazabicyclo[5,4,0]-7-undecene can be illustrated. As the palladium catalyst [1,1-bis (diphenylphosphino) ferrocene]-palladium (II) dichloride-dichloromethane complex (1:1), tetrakis(triphenylphosphine)palladium(0) and the like can be illustrated. The reaction temperature is usually at 0° C. to reflux temperature. The reaction time is usually from 30 minutes to 7 days, varying based on a used starting material, solvent and reaction temperature or the like.

The above coupling reaction can also be conducted by using a microwave reactor (Biotage). When a microwave reactor is used, the reaction is conducted at pressure range: 1 to 30 bar, power range: 1 to 400 W, reaction temperature: room temperature to 300° C., and reaction time: a minute to 1 day, varying based on a used starting material, solvent and model.

In addition, when a protective group is required for functional group of $R^1$ or $R^2$, the above coupling reaction can also be conducted after introduction of protective group.

Process 4

A compound represented by the formula (I) can also be prepared by conducting reduction such as catalytic reduction method of the olefin of Compound (8). The catalytic reduction method can be conducted, for example, by allowing Compound (8) to react by using a catalyst under a hydrogen gas atmosphere in an inert solvent. As the inert solvent, for example, methanol, ethanol, ethyl acetate, tetrahydrofuran and acetic acid can be illustrated. As the catalyst, for example, palladium-carbon powder, rhodium-carbon powder, platinum-carbon powder, platinum-carbon powder doped with vanadium can be illustrated. The reaction temperature is usually at room temperature to reflux temperature. The reaction time is usually from 30 minutes to 7 days, varying based on a used starting material, solvent and reaction temperature or the like.

In addition, when a protective group was introduced into functional group in the above step 3, a compound represented by the formula (I) can also be prepared by conducting deprotection reaction after the above reduction reaction.

Scheme 2

[Chem. 17]

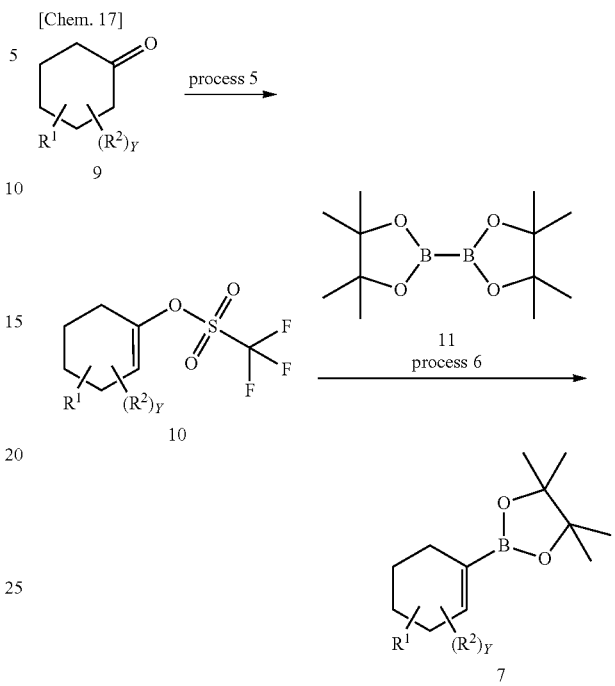

In the formula, $R^1$, $R^2$ and Y have the same meanings as defined above.

Process 5

Compound (10) can also be prepared by conducting reaction of Compound (9) with trifluoromethanesulfonic anhydride in an inert solvent in the presence of a base. As the inert solvent, for example, N,N-dimethylformamide, N-methylpyrrolidone, dimethylsulfoxide, diethyl ether, tetrahydrofuran, 1,4-dioxane, 1,2-dimethoxyethane, benzene, toluene, xylene, and a mixed solvent thereof can be illustrated. As the base, for example, potassium carbonate, sodium carbonate, cesium carbonate, sodium hydroxide, potassium hydroxide, lithium hydroxide, potassium fluoride, cesium fluoride, triethylamine, pyridine, N,N-diisopropylethylamine, 2,6-lutidine, 2,6-Di-tert-butyl-4-methylpyridine and 1,8-diazabicyclo[5,4,0]-7-undecene can be illustrated. The reaction temperature is usually at 0° C. to reflux temperature. The reaction time is usually from 30 minutes to 7 days, varying based on a used starting material, solvent and reaction temperature or the like.

Process 6

Compound (7) can also be prepared by conducting coupling reaction of Compound (10) with Compound (11) in an inert solvent in the presence of a base and a palladium catalyst. As the inert solvent, for example, N, N-dimethylformamide, N-methylpyrrolidine, dimethylsulfoxide, diethyl ether, tetrahydrofuran, 1,4-dioxane, 1,2-dimethoxyethane, benzene, toluene, xylene, and a mixed solvent thereof can be illustrated. As the base, for example, potassium carbonate, potassium acetate, sodium carbonate, cesium carbonate, sodium hydroxide, potassium hydroxide, lithium hydroxide, potassium fluoride, cesium fluoride, triethylamine, pyridine, N,N-diisopropylethylamine, 2,6-lutidine, and 1,8-diazabicyclo[5,4,0]-7-undecene can be illustrated. As the palladium catalyst, for example, [1,1'-bis (diphenylphosphino) ferrocene]-palladium (II) dichloride-dichloromethane complex (1:1), bis(triphenylphosphine)

palladium(II) dichloride can be illustrated. The reaction temperature is usually at room temperature to reflux temperature. The reaction time is usually from 30 minutes to 7 days, varying based on a used starting material solvent and reaction temperature or the like.

The above-mentioned schemes are exemplary for preparing compounds represented by the formula (I) of the present invention and synthetic intermediates thereof. The above schemes can be changed or modified into schemes which a person ordinarily skilled in the art can easily understand.

In the above schemes, when a protective group is necessary based on variation of functional group, operations of introduction and remove can also be conducted optionally in combination according to a general method.

Compounds represented by the formula (I) of the present invention and intermediates thereof can also be isolated and purified, if required, according to conventional isolation and purification techniques well known to a person ordinarily skilled in the art in the relevant field, such as solvent extraction, crystallization, recrystallization, chromatography, preparative high performance liquid chromatography or the like.

The compounds of the present invention have an excellent $NK_1$ receptor antagonist activity, and thus can also be used as an agent for the prevention or treatment of various diseases mediated by $NK_1$ receptor. For example, the compounds of the present invention are useful as antiemetic agent, especially useful as preventive agent of cancer-chemotherapy (for example, cisplatin)-induced gastrointestinal symptom (for example, nausea and vomiting). Preferable compounds of the present invention are not only useful for acute cancer-chemotherapy-induced nausea and vomiting but also delayed cancer-chemotherapy-induced-nausea and vomiting.

In an embodiment, the compounds of the present invention have an excellent $NK_1$ receptor antagonist activity, and thus can also be used as an agent for the prevention of postoperative nausea and vomiting (PONV), nausea and vomiting associated with radiotherapy, morphine-induced vomiting or motion sickness, and the treatment of schizophrenia, social phobia, anxiety and depression, alcoholism, irritable bowel syndrome, ulcerative colitis, coughing, asthma, atopic dermatitis, psoriasis, pruritus, pain, migraine, tinnitus, benign prostatic hyperplasia, overactive bladder or urinary incontinence.

Pharmaceutical compositions of the present invention can be administered in various dosage forms depending on their usages. As such dosage forms, for example, powders, granules, fine granules, dry syrups, tablets, capsules, injections, liquids, ointments, suppositories and poultices can be illustrated, which are administered orally or parenterally.

Pharmaceutical compositions of the present invention can be prepared by using a compound represented by the formula (I) or a pharmaceutically acceptable salt thereof and at least one of a pharmaceutical additive. These pharmaceutical compositions can be formulated by admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a conventional formulation procedure depending upon their dosage forms.

When a pharmaceutical composition of the present invention is used in the prevention or treatment, the dosage of a compound represented by the formula (I) or a pharmaceutically acceptable salt thereof as the active ingredient is appropriately decided to depend on the age, sex, body weight, degree of disorders and treatment of each patient and the like. The dosage for an adult can be decided within the range of, for example, 0.1 to 1000 mg per day, 0.1 to 500 mg per day, 0.1 to 100 mg per day, or 0.1 to 50 mg per day in the case of oral administration, and the daily dose can be divided into one, two, three or four times per day and administered. And, the dosage for an adult can be decided within the range of, for example, 0.1 to 1000 mg per day, 0.1 to 500 mg per day, 0.1 to 100 mg per day, or 0.1 to 50 mg per day in the case of parenteral administration, and the daily dose can be divided into one, two, three or four times per day and administered.

When a pharmaceutical composition of the present invention is used in the prevention of cancer-chemotherapy-induced nausea and vomiting, this pharmaceutical can also be administered before administration of antineoplastic agents. For example, the pharmaceutical can be administered immediately before administration to before an hour and a half of the administration in chemotherapy, and after the second day, the pharmaceutical can also be administered in the morning.

In an embodiment, a compound represented by the formula (I) of the present invention or a pharmaceutically acceptable salt thereof can also be used in combination with any other medicament other than $NK_1$ receptor antagonists. As such other medicaments used in combination, for example, corticosteroid and 5-$HT_3$ receptor antagonist antiemetic agent can be illustrated.

When a compound represented by the formula (I) of the present invention or a pharmaceutically acceptable salt thereof are used in combination with the other medicament, it can be administered as a formulation comprising together with their active ingredients or as formulations each of which is separately formulated from each active ingredient. When separately formulated, these formulations can be administered separately or concurrently.

Furthermore, the dosage of the compound represented by the formula (I) of the present invention or a pharmaceutically acceptable salt thereof can be reduced depending on the dosage of the other medicaments used in combination.

EXAMPLES

The present invention is further illustrated in more detail by way of the following Reference Examples, Examples and Test Examples. However, the present invention is not limited thereto.

Reference Example 1

4-(4,4,5,5-Tetramethyl-[1,3,2]-dioxaborolan-2-yl) cyclohex-3-enecarboxylic Acid Ethyl Ester To a solution of 4-oxocyclohexanecarboxylic acid ethyl ester (1.00 g) and 2,6-di-tert-butyl-4-methylpyridine (1.39 g) in dichloromethane (40 mL) was added trifluoromethanesulfonic anhydride (1.74 g) at room temperature, and the mixture was stirred at room temperature for 16 hours. The insoluble material was removed by filtration, and then washed with dichloromethane (5 mL). The filtrate was concentrated under reduced pressure, and to the residue was added dichloromethane (5 mL). The insoluble material was removed by filtration, and then washed with dichloromethane (3 mL). The filtrate was concentrated under reduced pressure, and to the residue was added dichloromethane (3 mL). The insoluble material was removed by filtration, and then washed with dichloromethane (2 mL). The filtrate was concentrated under reduced pressure to give 4-trifluoromethanesulfonyloxy-cyclohex-3-enecarboylic acid ethyl ester (1.57 g). Under an argon gas atmosphere, a suspension of 4-trifluoromethanesulfonyloxy-cyclohex-3-enecarboxylic acid ethyl ester (1.57 g), bis(pinacolato)diboran (1.39 g), [1,1'-bis(diphenylphosphino)ferrocene]palladium(II) dichloride dichloromethane complex (1:1) (0.13 g) and potassium acetate (1.53 g) in dimethyl sulfoxide (26 mL) was stirred at 50° C. for 4.5 hours. The reaction mixture was cooled to room temperature and water was added. The resulting mixture was extracted with ethyl acetate. The organic layer was washed with brine, and dried over anhydrous magnesium sulfate, and the solvent was removed under reduced pressure. The obtained crude product was purified by column chromatography on aminopropylsilylated silica gel (eluent: n-hexane/ethyl acetate=100/0-85/15) to give the title compound (0.84 g).

Reference Examples 2 to 7

The compounds of Reference Examples 2 to 7 were prepared in a similar manner to that described in Reference Example 1 using the corresponding starting materials.

Reference Example 8

(6-Chloro-4-iodopyridin-3-yl)carbamic Acid tert-butyl Ester

Under an argon gas atmosphere, to a solution of (6-chloropyridin-3-yl)carbamic acid tert-butyl ester (5.0 g) and N,N,N N'-tetramethylethane-1,2-diamine (7.7 g) in diethyl ether (120 mL) was added dropwise n-butyllithium (2.65 mol/L tetrahydrofuran solution, 25 mL) at −78° C. After the mixture was stirred at −10° C. for 2 hours, to the mixture was added dropwise a solution of iodine (11.4 g) in diethyl ether (40 mL) at −78° C., and the resulting mixture was stirred at room temperature for 1 day.

To the reaction mixture was added a saturated aqueous ammonium chloride solution, and the resulting mixture was extracted with diethyl ether. The organic layer was washed with 10% aqueous sodium pyrosulphite solution and brine, and dried over anhydrous magnesium sulfate, and the solvent was removed under reduced pressure. The obtained crude product was purified by column chromatography on silica gel (eluent: n-hexane/ethyl acetate=100/0-60/40) to give the title compound (2.59 g).

Reference Example 9

(6-Chloro-4-iodopyridin-3-yl)methylcarbamic Acid tert-butyl Ester

To a solution of (6-chloro-4-iodopyridin-3-yl)carbamic acid tert-butyl ester (2.59 g) in N,N-dimethylformamide (30 mL) was added sodium hydride (60%, 0.32 g) under ice-cooling, and the mixture was stirred at room temperature for 30 minutes. To the mixture was added iodomethane (2.60 g) under ice-cooling and the mixture was stirred at room temperature overnight. To the reaction mixture was added a saturated aqueous sodium hydrogen carbonate solution, and the resulting mixture was extracted with ethyl acetate. The organic layer was washed with water and brine, and dried over anhydrous magnesium sulfate, and the solvent was removed under reduced pressure. The obtained crude product was purified by column chromatography on aminopropylsilylated silica gel (eluent: n-hexane ethyl acetate=100/0-70/30) to give the title compound (2.66 g).

Reference Example 10

(6-Chloro-4-iodopyridin-3-yl)methylamine

To a solution of (6-chloro-4-iodopyridin-3-yl)methylcarbamic acid tert-butyl ester (2.66 g) in dichloromethane (10 mL) was added trifluoroacetic acid (8.23 g) under ice-cooling, and the mixture was stirred at room temperature for 2 hours. The reaction mixture was concentrated under reduced pressure, and to the residue was added a saturated aqueous sodium carbonate solution, and the mixture was extracted with ethyl acetate. The organic layer was washed with water and brine, and dried over anhydrous magnesium sulfate. The solvent was concentrated under reduced pressure to give the title compound (1.89 g).

Reference Example 11

[6-Chloro-4-(4-fluoro-2-methylphenyl)pyridin-3-yl]methylamine

To a mixture of (6-chloro-4-iodopyridin-3-yl)methylamine (1.89 g), 4-fluoro-2-methylphenyl boronic acid (1.30 g), 1,2-dimethoxyethane (20 mL) and water (20 mL) were added palladium (II) acetate (0.16 g), triphenylphosphine (0.37 g) and sodium carbonate (3.73 g) at room temperature, and the mixture was stirred at 90° C. overnight. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on aminopropylsilylated silica gel (eluent: n-hexane/ethyl acetate=100/0-50/50) to give the title compound (1.56 g).

Reference Example 12

(6-Chloro-4-ortho-tolylpyridin-3-yl)methylamine

To a mixture of (6-chloro-4-iodopyridin-3-yl)methylamine (0.70 g), 2-methylphenyl boronic acid (0.42 g), 1,2-dimethoxyethane (10 mL) and water (10 mL) were added palladium (II) acetate (0.058 g), triphenylphosphine (0.14 g) and sodium carbonate (1.38 g) at room temperature, and the mixture was stirred at 90° C. overnight. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane ethyl acetate=100/0-70/30) to give the title compound (0.54 g).

Reference Example 13

6-Chloro-3-nitropyridine-2-carbonitrile

To a solution of 2,6-dichloro-3-nitropyridine (2.50 g) in N-methylpyrrolidone (25 mL) was added copper (I) cyanide (2.32 g) at room temperature, and the mixture was stirred at 180° C. for 1 hour. The reaction mixture was cooled to room temperature, and to the mixture were added ethyl acetate and water. The insoluble material was removed by filtration. The filtrate was washed with brine, and the separated aqueous layer was re-extracted with ethyl acetate. The combined organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-70/30) to give the title compound (0.90 g).

Reference Example 14

3-Amino-6-chloropyridine-2-carbonitrile

To a solution of 6-chloro-3-nitropyridine-2-carbonitrile (0.32 g) and concentrated hydrochloric acid (1.2 mL) in ethanol (3.6 mL) was added iron powder (0.34 g) at room temperature, and the mixture was heated at reflux for 30 minutes. The reaction mixture was cooled to room temperature, and basified by the addition of saturated aqueous sodium hydrogen carbonate solution. To the reaction mixture was added ethyl acetate, and the resulting mixture was filtered through a Celite (registered trademark) pad. The filtrate was extracted with ethyl acetate. The organic layer was washed with water and brine, and dried over anhydrous magnesium sulfate. The solvent was concentrated under reduced pressure to give the title compound (0.24 g).

Reference Example 15

3-Amino-bromo-6-chloropyridine-2-carbonitrile

To a solution of 3-amino-6-chloropyridine-2-carbonitrile (0.24 g) in N,N-dimethylformamide (8 mL) was added N-bromosuccinimide (0.37 g) at room temperature, and the mixture was stirred at the same temperature overnight. To the reaction mixture was added saturated aqueous sodium thiosulfate solution, and the resulting mixture was extracted with ethyl acetate. The organic layer was washed with brine, and dried over anhydrous magnesium sulfate, and the solvent was removed under reduced pressure. The obtained crude product was purified by column chromatography on aminopropylsilylated silica gel (eluent:n-hexane/ethyl acetate=75/25-50/50) to give the title compound (0.30 g).

Reference Example 16

3-Amino-6-chloro-4-(4-fluoro-2-methylphenyl)pyridine-2-carbonitrile

A mixture of 3-amino-4-bromo-6-chloropyridine-2-carbonitrile (0.15 g), 4-fluoro-2-methylphenylboronic acid (0.08 g), tetrakis(triphenylphospine)palladium(0) (0.07 g), sodium carbonate (0.20 g), 1,2-dimethoxyethane (3.2 mL) and water (0.8 mL) was stirred at 100° C. under microwave irradiation for 1 hour. The reaction mixture was cooled to room temperature and water was added. The resulting mixture was extracted with ethyl acetate. The organic layer was washed with saturated aqueous sodium hydrogen carbonate solution and brine, and dried over anhydrous magnesium sulfate, and the solvent was removed under reduced pressure. The obtained crude product was purified by column chromatography on aminopropylsilylated silica gel (eluent: n-hexane/ethyl acetate=50/50-0/100) to give the title compound (0.14 g).

Reference Example 17

3-Benzyloxy-2-(3,5-bistrifluoromethylphenyl)-2-methylpropionic Acid

Under an argon gas atmosphere, to a solution of 2-(3,5-bistrifluoromethylphenyl)propionic acid methyl ester (0.60 g) in tetrahydrofuran (5 mL) was added dropwise lithium diisopropylamide (1.09 mol/L tetrahydrofuran/n-hexane solution, 2 mL) al −78° C., and the mixture was stirred at the same temperature for 15 minutes. To the reaction mixture was added a solution of benzyl chloromethyl ether (0.34 g) in tetrahydrofuran (2 mL) at −78° C., and the mixture was stirred at room temperature for 1 hour. To the reaction mixture was added a saturated aqueous ammonium chloride solution, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-70/30) to give 3-benzyloxy-2-(3,5-bistrifluoromethylphenyl)-2-methylpropionic acid methyl ester (0.78 g). To a solution of the obtained compound (0.78 g) in ethanol (3 mL) was added 5.0 mol/L aqueous sodium hydroxide solution (1 mL) at room temperature, and the mixture was stirred at room temperature for 3 hours. To the reaction mixture was added 2.0 mol/L hydrochloric acid (3 ml), and the mixture was extracted with ethyl acetate. The organic layer was washed with water and brine, and dried over anhydrous magnesium sulfate. The solvent was removed under reduced pressure to give the title compound (0.77 g).

Reference Example 18

2-(3,5-Bistrifluoromethylphenyl)-N-[6-chloro-4-(4-fluoro-2-methylphenyl)pyridin-3-yl]-N-methylisobutylamide To a solution of 2-(3,5-bistrifluoromethylphenyl)-2-methylpropionic acid (0.66 g) in dichloromethane (10 mL) were added oxalyl chloride (0.56 g) and N,N-dimethylformamide (2 drops) at room temperature, and the mixture was stirred at the same temperature for 1 hour. The reaction mixture was concentrated under reduced pressure to give the residue. Under an argon gas atmosphere, to a solution of [6-chloro-4-(4-fluoro-2-methylphenyl)pyridin-3-yl]methylamine (0.50 g) in tetrahydrofuran (10 mL) was added dropwise potassium bis(trimethylsilyl)amide (0.5 mol/L toluene solution, 5.0 mL) under ice-cooling, and the mixture was stirred at room temperature for 30 minutes. To the reaction mixture was added dropwise a solution of the above residue in tetrahydrofuran (5 mL) under ice-cooling, and the mixture was stirred at room temperature for 2 hours. To the reaction mixture was added 1.0 mol/L aqueous sodium hydrogen carbonate solution, and the mixture was extracted with ethyl acetate. The organic layer was washed with water and brine, and dried over anhydrous magnesium sulfate, and the solvent was removed under reduced pressure. The obtained crude product was purified by column chromatography on aminopropylsilylated silica gel (eluent: n-hexane/ethyl acetate=100/0-60/40) to give the title compound (1.03 g).

Reference Examples 19 and 20

The compounds of Reference Examples 19 and 20 were prepared in a similar manner to that described in Reference Example 18 using the corresponding starting materials.

Reference Example 21

2-(3,5-Bistrifluoromethylphenyl)-N-[6-chloro-2-cyano-4-(4-fluoro-2-methylphenyl)pyridin-3-yl]isobutylamide To a solution of 2-(3,5-bistrifluoromethylphenyl)-2-methylpropionic acid (0.31 g) in dichloromethane (2.6 mL) were added oxalyl chloride (0.26 g) and N,N-dimethylformanide (2 drops) at room temperature, and the mixture was stirred at the same temperature for 1 hour. The reaction mixture was concentrated under reduced pressure to give the residue. To a solution of 3-amino-6-chloro-4-(4-fluoro-2-methylphenyl)pyridine-2-carbonitrile (0.14 g) in tetrahydrofuran (5 mL) was added sodium bis(trimethylsilyl)amide (1.0 mol/L tetrahydrofuran solution, 1.1 mL) under ice-cooling, and the mixture was stirred at the same temperature for 30 minutes. To the reaction mixture was added dropwise a solution of the above residue in tetrahydrofuran (2.0 mL) under ice-cooling, and the mixture was stirred at room temperature for 30 minutes. To the reaction mixture was added a saturated aqueous sodium hydrogen carbonate solution, and the resulting mixture was extracted with ethyl acetate. The organic layer was washed with water and brine, and dried over anhydrous magnesium sulfate, and the solvent was removed under reduced pressure. The obtained crude product was purified by column chromatography on aminopropylsilylated silica gel (eluent: n-hexane/ethyl acetate=85/15-40/60) to give the title compound (0.21 g).

Reference Example 22

2-(3,5-Bistrifluoromethylphenyl)-N-[6-chloro-2-cyano-4-(4-fluoro-2-methylphenyl)pyridin-3-yl]-N-methylisobutylamide To a solution of 2-(3,5-bistrifluoromethylphenyl)-N-[6-chloro-2-cyano-4-(4-fluoro-2-methylphenyl)pyridin-3-yl]isobutylamide (0.21 g) in N,N-dimethylformamide (2.4 mL) was added sodium hydride (60%. 0.018 g) under ice-cooling, and the mixture was stirred at the same temperature for 5 minutes. To the reaction mixture was added iodomethane (0.11 g) under ice-cooling, and the mixture was stirred at room temperature overnight. To the reaction mixture was added water, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-50/50) to give the title compound (0.09 g).

Reference Example 23

4-[5-{[3,5-Bistrifluoromethylphenyl)-2-methylpropionyl]methylamino}-4-(4-fluoro-2-methylphenyl)pyridin-2-yl]cyclohex-3-enecarboxylic Acid Ethyl Ester A mixture of 2-(3,5-bistrifluoromethylphenyl)-N-[6-chloro-4-(4-fluoro-2-methylphenyl)pyridin-3-yl]-N-methylisobutylamide (0.08 g), 4-(4,4,5,5-tetramethyl-[1,3,2]-dioxaborolan-2-yl)cyclohex-3-enecarboxylic acid ethyl ester (0.08 g), sodium carbonate (0.05 g), tetrakis(triphenylphosphine)palladium(0) (0.02 g), 1,2-dimethoxyethane (1.0 mL), water (0.2 mL) and ethanol (0.2 mL) was stirred at 120° C. under microwave irradiation for 1 hour. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on aminopropylsilylated silica gel (eluent; n-hexane/ethyl acetate=100/0-80/20) to give the title compound (0.03 g).

Reference Examples 24 to 26

The compounds of Reference Examples 24 to 26 were prepared in a similar manner to that described in Reference Example 23 using the corresponding starting materials.

Reference Example 27

2-(3,5-Bistrifluoromethylphenyl)-N-[6-(1,4-dioxaspiro[4.5]dec-7-en-8-yl)-4-(4-fluoro-2-methylphenyl)pyridin-3-yl]-N-methylisobutylamide A mixture of 2-(3,5-bistrifluoromethylphenyl)-N-[6-chloro-4-(4-fluoro-2-methylphenyl)pyridin-3-yl]-N-methylisobutylamide (0.53 g), 8-(4,4,5,5-tetramethyl-[1,3,2]-dioxaborolan-2-yl)-1,4-dioxaspiro[4.5]dec-7-ene (0.29 g), sodium carbonate (0.32 g), tetrakis(triphenylphosphine)palladium(0) (0.12 g). 1,2-dimethoxyethane (7.5 mL), water (1.5 mL) and ethanol (1.5 mL) was stirred at 120° C. under microwave irradiation for 30 minutes. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane ethyl acetate=90/10-10/90) to give the title compound (0.52 g).

Reference Examples 28 to 30

The compounds of Reference Examples 28 to 30 were prepared in a similar manner to that described in Reference Example 23 using the corresponding starting materials.

Reference Example 31

2-{4-[5-{[2-(3,5-Bistrifluoromethylphenyl)-2-methylpropionyl]methylamino}-4-(4-fluoro-2-methylphenyl)pyridin-2-yl]cyclohex-3-enyl}-2-methylpropionic Acid Ethyl Ester A mixture of 2-(3,5-bistrifluoromethylphenyl)-N-[6-chloro-4-(4-fluoro-2-methylphenyl)pyridin-3-yl]-N-methylisobutylamide (0.11 g), 2-methyl-2-[4(4,4,5,5-tetramethyl [1,3,2]dioxaborolan-2-yl)cyclohex-3-enyl]propionic acid ethyl ester (0.12 g), sodium carbonate (0.06 g), tetrakis(triphenylphosphine)palladium(0) (0.02 g), 1,2-dimethoxyethane (1.5 mL), water (0.3 mL) and ethanol (0.3 mL) was stirred at 120° C. under microwave irradiation for 30 minutes. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatog-

Reference Example 32

{4-[5-{[2-(3,5-Bistrifluoromethylphenyl)-2-methyl-propionyl]methylamino}-4-(4-fluoro-2-methylphenyl)pyridin-2-yl]cyclohex-3-enyl}acetic Acid Methyl Ester A mixture of 2-(3,5-bistrifluoromethylphenyl)-N-[6-chloro-4-(4-fluoro-2-methylphenyl)pyridin-3-yl]-N-methylisobutylamide (2.00 g), [4-(4,4,5,5-tetramethyl[1,3,2]dioxaborolan-2-yl)cyclohex-3-enyl]acetic acid methyl ester (1.26 g), tetrakis(triphenylphospine)palladium(0) (0.22 g), 2.0 mol/L aqueous sodium carbonate solution (5.6 mL), 1,2-dimethoxyethane (22.5 mL) and ethanol (5.6 mL) was stirred at 120° C. under microwave irradiation for 30 minutes. The reaction mixture was cooled to room temperature and water was added. The resulting mixture was extracted with ethyl acetate. The organic layer was washed with brine, and dried over anhydrous magnesium sulfate, and the solvent was removed under reduced pressure. The obtained crude product was purified by column chromatography on aminopropylsilylated silica gel (eluent: n-hexane/ethyl acetate=100/0-50/50) to give the title compound (2.14 g).

Reference Example 33

2-(3,5-Bistrifluoromethylphenyl)-N-[4-(4-fluoro-2-methylphenyl)-6-(1-methyl-3-oxocyclohexyl)pyridin-3-yl]-N-methylisobutylamide To a suspension of copper (I) iodide (0.05 g) in diethyl ether (2 mL) was added methyllithium (1.13 mol/L diethyl ether solution, 0.45 mL) under ice-cooling, and the mixture was stirred at the same temperature for 15 minutes. To the reaction mixture was added drop wise 2-(3,5-bistrifluoromethylphenyl)-N-[4-(4-fluoro-2-methylphenyl)-6-(3-oxocyclohex-1-enyl)pyridin-3-yl]-N-methylisobutylamide (0.10 g) in diethyl ether (1 mL) under ice-cooling, and the mixture was stirred at room temperature for 1 hour. To the reaction mixture was added a saturated aqueous ammonium chloride solution, and the resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=85/15-50/50) to give the title compound (0.50 g).

Reference Example 34

{3-[5-{[2-(3,5-Bistrifluoromethylphenyl)-2-methyl-propionyl]methylamino}-4-(4-fluoro-2-methylphenyl)pyridin-2-yl]cyclohex-2-enylidene}acetic Acid Ethyl Ester To a suspension of sodium hydride (60%, 0.012 g) in tetrahydrofuran (2 mL) was added diethyl phosphonoacetate (0.08 g) under ice-cooling, and the mixture was stirred at the same temperature for 30 minutes. To the reaction mixture was added 2-(3,5-bistrifluoromethylphenyl)-N-[4-(4-fluoro-2-methylphenyl)-6-(3-oxocyclohex-1-enyl)pyridin-3-yl]N-methylisobutylamide (0.10 g) in tetrahydrofuran (1 mL) at room temperature, and the mixture was stirred at the same temperature overnight and at 50° C. for 24 hours. The reaction mixture was cooled to room temperature and water was added. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=85/15-40/60) to give the title compound (0.05 g).

Reference Example 35

The compound of Reference Example 35 was prepared in a similar manner to that described in Reference Example 34 using the corresponding starting material.

Reference Example 36

2-(3,5-Bistrifluoromethylphenyl)-N-[6-(1,4-dioxaspiro[4.5]dec-8-yl)-4-(4-fluoro-2-methylphenyl)pyridin-3-yl]-N-methylisobutylamide Under a hydrogen gas atmosphere, a suspension of 2-(3,5-bistrifluoromethylphenyl)-N-[6-(1,4-dioxaspiro[4.5]dec-7-en-8-yl)-4-(4-fluoro-2-methylphenyl)pyridin-3-yl]-N-methylisobutylamide (0.52 g) and 10% palladium on carbon (0.10 g, wet) in methanol (10 mL) was stirred at room temperature overnight. The reaction mixture was filtered through a Celite (registered trademark) pad, and the filtrate was concentrated under reduced pressure to give the title compound (0.50 g).

Reference Example 37

2-(3,5-Bistrifluoromethylphenyl)-N-[4-(4-fluoro-2-methylphenyl)-6-(4-oxocyclohexyl)pyridin-3-yl]-N-methylisobutylamide To a solution of 2-(3,5-bistrifluoromethylphenyl)-N-[6-(1,4-dioxaspiro[4.5]dec-8-yl)-4-(4-fluoro-2-methylphenyl)pyridin-3-yl]-N-methylisobutylamide (0.50 g) in acetone was added 1.0 mol/L hydrochloric acid (3.0 mL) at room temperature, and the mixture was stirred at 50° C. for 2 hours. The reaction mixture was cooled to room temperature and water was added. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=90/10-10/90) to give the title compound (0.41 g).

Reference Example 38

{4-[5-{[2-(3,5-Bistrifuoromethylphenyl)-2-methyl-propionyl]methylamino}-4-(4-fluoro-2-methylphenyl)pyridin-2-yl]-1-hydroxycyclohexyl}acetic Acid Ethyl Ester Under an argon gas atmosphere, to a solution of ethyl acetate (0.021 g) in tetrahydrofuran (1 mL) was added dropwise lithium diisopropylamide solution (1.09 mol/L tetrahydrofuran/n-hexane solution, 0.20 mL) at −78° C., and the mixture was stirred at the same temperature for 20 minutes. To the reaction mixture was added a solution of 2-(3,5-bistrifluoromethylphenyl)-N-[4-(4-fluoro-2-methylphenyl)-6-(4-oxocyclohexyl)pyridin-3-yl]-N-methylisobutylamide (0.10 g) in tetrahydrofuran (1 mL) at −78° C., and the mixture was stirred at room temperature for 2 hours. To the reaction mixture was added a saturated aqueous ammonium chloride solution, and the resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-10/90) to give the title compound (0.10 g).

Reference Example 39

2-{4-[5-{[2-(3,5-Bistrifluoromethylphenyl)-2-methylpropionyl]methylamino}-4-(4-fluoro-2-methylphenyl)pyridin-2-yl]cyclohexylidene}propionic Acid Ethyl Ester To a suspension of sodium hydride (60%, 0.017 g) in tetrahydrofuran (2 mL) was added 2-phosphonopropionic acid triethyl ester (0.11 g) under ice-cooling, and the mixture was stirred at the same temperature for 30 minutes. To the reaction mixture was added a solution of 2-(3,5-bistrifluoromethylphenyl)-N-[4-(4-fluoro-2-methylphenyl)-6-(4-oxocyclohexyl)pyridin-3-yl]-N-methylisobutylamide (0.14 g) in tetrahydrofuran (1 mL) at room temperature, and the mixture was stirred at 50° C. overnight. The reaction mixture was cooled to room temperature and a saturated aqueous ammonium chloride solution was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=100/0-50/50) to give the title compound (0.13 g).

Reference Example 40

{3-[5-{[2-(3,5-Bistrifluoromethylphenyl)-2-methylpropionyl]methylamino}-4-(4-fluoro-2-methylphenyl)pyridin-2-yl]cyclohexyl}acetic Acid Ethyl Ester Under a hydrogen gas atmosphere, a suspension of {3-[5-{[2-(3,5-bistrifluoromethylphenyl)-2-methylpropionyl]methylamino}-4-(4-fluoro-2-methylphenyl)pyridin-2-yl]cyclohex-2-enylidene}acetic acid ethyl ester (0.03 g) and 10% palladium on carbon (0.01 g, wet) in methanol (1 mL) was stirred at room temperature overnight. The reaction mixture was filtered through a Celite (registered trademark) pad, and the filtrate was concentrated under reduced pressure. The obtained crude product was purified by column chromatography on silica gel (eluent: n-hexane/ethyl acetate=85/15-40/60) to give the title compound (0.02 g).

Reference Example 41

The compound of Reference Example 41 was prepared in a similar manner to that described in Reference Example 40 using the corresponding starting material.

Reference Example 42

2-{4-[5-{[2-(3,5-Bistrifluoromethylphenyl)-2-methylpropionyl]methylamino}-4-(4-fluoro-2-methylphenyl)pyridin-2-yl]cyclohexyl}propionic Acid Ethyl Ester Under a hydrogen gas atmosphere, a suspension of 2-{4-[5-{[2-(3,5-bistrifluoromethylphenyl)-2-methylpropionyl]methylamino}-4-(4-fluoro-2-methylphenyl)pyridin-2-yl]cyclohexylidene}propionic acid ethyl ester (0.13 g) and 10% palladium on carbon (0.025 g, wet) in methanol (5 mL) was stirred at room temperature overnight. The reaction mixture was filtered through a Celite (registered trademark) pad, and the filtrate was concentrated under reduced pressure to give the title compound (0.11 g).

Reference Example 43

4-[5-{[3,5-Bistrifluoromethylphenyl)-2-methylpropionyl]methylamino}-4-(4-fluoro-2-methylphenyl)pyridin-2-yl]cyclohexanecarboxylic Acid Ethyl Ester Under a hydrogen gas atmosphere, a suspension of 4-[5-{[2-(3,5-bistrifluoromethylphenyl)-2-methylpropionyl]methylamino}-4-(4-fluoro-2-methylphenyl)pyridin-2-yl]cyclohex-3-enecarboxylic acid ethyl ester (0.03 g) and 10% palladium on carbon (0.010 g, wet) in ethanol (1 mL) was stirred at room temperature for 14 hours. The reaction mixture was filtered through a Celite (registered trademark) pad, and the filtrate was concentrated under reduced pressure. The obtained crude product was purified by column chromatography on silica gel (eluent: n-hexane/ethyl acetate=70/30-50/50) to give the title compound (0.02 g).

Reference Examples 44 to 47

The compounds of Reference Examples 44 to 47 were prepared in a similar manner to that described in Reference Example 43 using the corresponding starting materials.

Reference Example 48

{4-[5-{[3-Benzyloxy-2-(3,5-bistrifluoromethylphenyl)-2-methylpropionyl]methylamino}-4-(4-fluoro-2-methylphenyl)pyridin-2-yl]cyclohex-3-enyl}acetic Acid To a mixture of {4-[5-{[3-benzyloxy-2-(3,5-bistrifluoromethylphenyl)-2-methylpropionyl]methylamino}-4-(4-fluoro-2-methylphenyl)pyridin-2-yl]cyclohex-3-enyl}acetic acid ethyl ester (0.11 g), tetrahydrofuran (1 mL), methanol (0.5 mL) and water (0.5 mL) was added lithium hydroxide monohydrate (0.03 g) at room temperature, and the mixture was stirred at the same temperature overnight. To the reaction mixture was added 2.0 mol/L hydrochloric acid (0.4 mL), and the solvent was removed under reduced pressure. To the residue was added water, and extracted with ethyl acetate. The organic layer was washed with water and brine, and dried over anhydrous magnesium sulfate, and the solvent was removed under reduced pressure. The obtained crude product was purified by column chromatography on silica gel (eluent: ethyl acetate/methanol=100/0-90/10) to give the title compound (0.05 g).

Reference Examples 49 and 50 trans-2-{4-[5-{[2-(3,5-Bistrifluoromethylphenyl)-2-methylpropionyl]methylamino}-4-(4-fluoro-2-methylphenyl)pyridin-2-yl]cyclohexyl}-2-methylpropionic acid ethyl ester (Reference Example 49), and cis-2-{4-[5-{[2-(3,5-bistrifluoromethylphenyl)-2-methylpropionyl]methylamino}-4-(4-fluoro-2-methylphenyl)pyridin-2-yl]cyclohexyl}-2-methylpropionic acid ethyl ester (Reference Example 50)

Under a hydrogen gas atmosphere, a mixture of 2-{4-[5-{[2-(3,5-bistrifluoromethylphenyl)-2-methylpropionyl]

methylamino}-4-(4-fluoro-2-methylphenyl)pyridin-2-yl]cyclohex-3-enyl}-2-methylpropionic acid ethyl ester (0.11 g), 10% palladium on carbon (0.03 g, wet), methanol (2 mL) and tetrahydrofuran (1 mL) was stirred at room temperature overnight. The reaction mixture was filtered through a Celite (registered trademark) pad, and the filtrate was concentrated under reduced pressure. The obtained crude product was purified by column chromatography on silica gel (eluent: n-hexane/ethyl acetate=100/0-60/40) to give Reference Examples 49 (0.05 g) and Reference Examples 50 (0.04 g). In the above chromatography, the compound of Reference Examples 49 was in the high polarity side, and the compound of Reference Examples 50 was in the low polarity side.

Reference Example 51

{4-[5-{[2-(3,5-Bistrifluoromethylphenyl)-2-methylpropionyl]methylamino}-4-(4-fluoro-2-methylphenyl)pyridin-2-yl}cyclohexyl]acetic Acid Methyl Ester Under a hydrogen gas atmosphere, a suspension of {4-[5-{[2-(3,5-bistrifluoromethylphenyl)-2-methylpropionyl]methylamino}-4-(4-fluoro-2-methylphenyl)pyridin-2-yl]cyclohex-3-enyl}acetic acid methyl ester (2.14 g) and 10% palladium on carbon (E101 NE/W type (EVONIK))(0.21 g) in methanol (96 mL) was stirred at room temperature overnight. The reaction mixture was filtered through a Celite (registered trademark) pad, and the filtrate was concentrated under reduced pressure. The obtained crude product was purified by column chromatography on aminopropylsilylated silica gel (eluent: n-hexane/ethyl acetate=100/0-40/60) to give the title compound (2.13 g).

Reference Example 52

{4-[5-{[2-(3,5-Bistrifluoromethylphenyl)-2-methylpropionyl]methylamino}-4-(4-fluoro-2-methylphenyl)pyridin-2-yl]-1-methylcyclohexyl}acetic Acid Methyl Ester To a suspension of sodium hydride (60%, 0.020 g) in tetrahydrofuran (2 mL) was added dimethyl phosphonoacetic acid methyl ester (0.09 g) under ice-cooling, and the mixture was stirred at room temperature for 1 hour. To the reaction mixture was added a solution of 2-(3,5-bistrifluoromethylphenyl)-N-[4-(4-fluoro-2-methylphenyl)-6-(4-oxocyclohexyl)pyridin-3-yl]-N-methylisobutylamide (0.15 g) in tetrahydrofuran (1 mL) at room temperature, and the mixture was stirred at 50° C. for 30 minutes. The reaction mixture was cooled to room temperature and a saturated aqueous ammonium chloride solution was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-30/70) to give {4-[5-{[2-(3,5-bistrifluoromethylphenyl)-2-methylpropionyl]methylamino}-4-(4-fluoro-2-methylphenyl)pyridin-2-yl]cyclohexylidene}acetic acid methyl ester (0.15 g).

To a suspension of copper (I) iodide (0.05 g) in diethyl ether (0.40 mL) was added methyllithium (1.13 mol/L diethyl ether solution, 0.50 mL) under ice-cooling, and the mixture was stirred at the same temperature for 10 minutes, and the solvent was concentrated under reduced pressure. Under an argon gas atmosphere, to the residue was added dichloromethane (0.40 mL) under ice-cooling, and the mixture was stirred for 5 minutes, and the solvent was concentrated under reduced pressure. To the residue was added dichloromethane (0.40 mL), and cooled to −78° C. To the mixture was added trimethylsilyl chloride (0.03 g), and to the resulting mixture was added dropwise a solution of {4-[5-{[2-(3,5-bistrifluoromethylphenyl)-2-methylpropionyl]methylamino}-4-(4-fluoro-2-methylphenyl)pyridin-2-yl]cyclohexylidene}acetic acid methyl ester (0.09 g) in dichloromethane (1.0 mL). The resulting mixture was stirred under ice-cooling for 1 hour and at room temperature overnight. To the reaction mixture was added a saturated aqueous ammonium chloride solution, and the resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent, n-hexane/ethyl acetate=90/10-40/60) to give the title compound (0.08 g).

Reference Example 53

The compound of Reference Example 53 was prepared in a similar manner to that described in Reference Example 16 using the corresponding starting material.

Reference Example 54

The compound of Reference Example 54 was prepared in a similar manner to that described in Reference Example 21 using the corresponding starting material.

Reference Example 55

The compound of Reference Example 55 was prepared in a similar manner to that described in Reference Example 22 using the corresponding starting material.

Reference Examples 56 and 57

The compounds of Reference Examples 56 and 57 were prepared in a similar manner to that described in Reference Example 23 using the corresponding starting materials.

Reference Examples 58 and 59

The compounds of Reference Examples 58 and 59 were prepared in a similar manner to that described in Reference Example 43 using the corresponding starting materials.

Reference Example 60

{4-[5-{[2-(3,5-Bistrifluoromethylphenyl)-2-methylpropionyl]methylamino}-4-(4-fluoro-2-methylphenyl)-1-oxypyridin-2-yl]cyclohexyl}acetate Acid Ethyl Ester To a solution of {4-[5-{[2-(3,5-bistrifluoromethylphenyl)-2-methylpropionyl]methylamino}-4-(4-fluoro-2-methylphenyl)-1-oxypyridin-2-yl]cyclohexyl}acetic acid ethyl ester (0.37 g) in dichloromethane was added m-chloroperoxybenzoic acid (purity 70%, 0.55 g) under ice-cooling, and the mixture was stirred at room temperature overnight. The reaction mixture was cooled with ice, and to the mixture was added 1.0 mol/L aqueous sodium hydroxide solution. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=40/60-0/100) to give the title compound (0.35 g).

Reference Example 61

{4-[5-{[2-(3,5-Bistrifluoromethylphenyl)-2-methylpropionyl]methylamino}-6-chloro-4-(4-fluoro-2-methylphenyl)pyridin-2-yl]cyclohexyl}acetic Acid Ethyl Ester A mixture of {4-[5-{[2-(3,5-bistrifluoromethylphenyl)-2-methylpropionyl]methylamino}-4-(4-fluoro-2-methylphenyl)-1-oxypyridin-2-yl]cyclohexyl}acetic acid ethyl ester (0.20 g) and phosphoryl chloride (0.60 mL) was stirred at 120° C. for 2 hours. The reaction mixture was cooled with ice, and basified by the addition of water and aqueous ammonia. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=90/10-50/50) to give the title compound (0.16 g).

Reference Example 62

{4-[5-{[2-(3,5-Bistrifluoromethylphenyl)-2-methylpropionyl]methylamino}-4-(4-fluoro-2-methylphenyl)-6-methylpyridin-2-yl]cyclohexyl}acetic Acid Ethyl Ester A mixture of {4-[5-{[2-(3,5-bistrifluoromethylphenyl)-2-methylpropionyl]methylamino}-6-chloro-4-(4-fluoro-2methylphenyl)pyridin-2-yl]cyclohexyl}acetic acid ethyl ester (0.04 g), 2,4,6-trimethylcyclotriboroxane (0.014 g), tetrakis(triphenylphospine)palladium(0) (0.007 g), sodium carbonate (0.016 g) and 1,2-dimethoxyethane (2.9 mL) was stirred at 120° C. under microwave irradiation for 1 hour. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=80/20-20/80) to give the tide compound (0.019 g).

Reference Example 63

{4-[5-{[2-(3,5-Bistrifluoromethylphenyl)-2-methylpropionyl]methylamino}-4-(4-fluoro-2-methylphenyl)-6-hydroxymethylpyridin-2-yl]cyclohexyl}acetic Acid Ethyl Ester To a solution of {4-[5-{[2-(3,5-bistrifluoromethylphenyl)-2-methylpropionyl]methylamino}-4-(4-fluoro-2-methylphenyl)-1-oxypyridin-2-yl]cyclohexyl}acetyl acid ethyl ester (0.15 g) in dichloromethane (2.0 mL) was added trimethyloxonium tetrafluoroborate (0.04 g) at room temperature, and the mixture was stirred at the same temperature for 2 hours. The reaction mixture was concentrated under reduced pressure, and to the residue was added methanol (2.0 mL). To the mixture was added a solution of ammonium persulfate (0.01 g) in water (0.02 mL) at 65° C., and the mixture was stirred at the same temperature for 1 hour. To the reaction mixture was added a solution of ammonium persulfate (0.01 g) in water (0.02 mL) at 65° C., and the mixture was stirred at the same temperature for 13 hours. After the reaction mixture was cooled to room temperature, the solvent was concentrated under reduced pressure. To the residue was added an aqueous solution of sodium carbonate, and the mixture was extracted with ethyl acetate. The organic layer was washed with brine, and dried over anhydrous magnesium sulfate. The solvent was concentrated under reduced pressure to give a mixture of the title compound and {4-[5-{[2-(3,5-bistrifluoromethylphenyl)-2-methylpropionyl]methylamino}-4-(4-fluoro-2-methylphenyl)-6-hydroxymethylpyridin-2-yl]cyclohexyl}acetic acid methyl ester (0.06 g).

Example 1

4-[5-{[2-(3,5-Bistrifluoromethylphenyl)-2-methylpropionyl]methylamino}-4-(4-fluoro-2-methylphenyl)pyridin-2-yl]cyclohexanecarboxylic Acid To a mixture of 4-[5-{[2-(3,5-bistrifluromethylphenyl)-2-methylpropionyl]methylamino}-4-(4-fluoro-2-methylphenyl)pyridin-2-yl]cyclohexanecarboxylic acid ethyl ester (0.022 g), tetrahydrofuran (0.375 mL), methanol (0.375 mL) and water (0.150 mL) was added lithium hydroxide monohydrate (0.014 g) at room temperature, and the mixture was stirred at the same temperature for 72 hours. To the reaction mixture were added 2.0 mol/L hydrochloric acid (0.170 mL) and water, and the resulting mixture was extracted with ethyl acetate. The organic layer was washed with water and brine, and dried over anhydrous sodium sulfate. The solvent was concentrated under reduced pressure to give the title compound (0.018 g).

Example 2

3-{4-[5-{[2-(3,5-Bistrifluoromethylphenyl)-2-methylpropionyl]methylamino}-4-(4-fluoro-2-methylphenyl)pyridin-2-yl]cyclohexyl}propionic Acid To a mixture of 3-{4-[5-{[2-(3,5-bistrifluoromethylphenyl)-2-methylpropionyl]methylamino}-4-(4-fluoro-2-methylphenyl)pyridin-2-yl]cyclohexyl}propionic acid ethyl ester (0.019 g), tetrahydrofuran (0.375 mL), methanol (0.375 mL) and water (0.150 mL) was added lithium hydroxide monohydrate (0.012 g) at room temperature, and the mixture was stirred at the same temperature for 6 hours. To the reaction mixture was added 2.0 mol/L hydrochloric acid (0.140 mL) and water, and the resulting mixture was extracted with ethyl acetate. The organic layer was washed with water and brine, and dried over anhydrous sodium sulfate. The solvent was concentrated under reduced pressure to give the title compound (0.017 g).

Example 3

{3-[5-{[2-(3,5-Bistrifluoromethylphenyl)-2-methylpropionyl]methylamino}-4-(4-fluoro-2-methylphenyl)pyridin-2-yl]cyclohexyl}acetic Acid To a mixture of {3-[5-{[2-(3,5-bistrifluoromethylphenyl)-2-methylpropionyl]methylamino}-4-(4-fluoro-2-methylphenyl)pyridin-2-yl]cyclohexyl}acetic acid ethyl ester (0.023 g), tetrahydrofuran (0.50 mL), methanol (0.25 mL) and water (0.25 mL) was added lithium hydroxide monohydrate (0.007 g) at room temperature, and the mixture was stirred at the same temperature overnight. The reaction mixture was neutralized by the addition of acetic acid. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate/methanol=50/50/0-0/100/0-0/90/10) to give the title compound (0.003 g).

Example 4

{3-[5-{[2-(3,5-Bistrifluoromethylphenyl)-2-methyl-propionyl]methylamino}-4-(4-fluoro-2-methylphenyl)pyridin-2-yl]-3-methylcyclohexyl}acetic Acid To a mixture of {3-[5-{[2-(3,5-bistrifluoromethylphenyl)-2-methylpropionyl]methylamino}4-(4-fluoro-2-methylphenyl)-pyridin-2-yl]-3-methylcyclohexyl}acetic acid ethyl ester (0.022 g), tetrahydrofuran (0.40 mL), methanol (0.20 mL) and water (0.20 mL) was added lithium hydroxide monohydrate (0.006 g) at room temperature, and the mixture was stirred at the same temperature overnight. The reaction mixture was neutralized by the addition of acetic acid. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate/methanol=50/50/0-0/100/0-0/90/10) to give the title compound (0.007 g).

Example 5

{4-[5-{[2-(3,5-Bistrifluoromethylphenyl)-3-hydroxy-2-methylpropionyl]methylamino}-4-(4-fluoro-2-methylphenyl)pyridin-2-yl]cyclohexyl}acetic Acid Under a hydrogen gas atmosphere, a suspension of {4-[5-{[3-benzyloxy-2-(3,5-bistrifluoromethylphenyl)-2-methylpropionyl]methylamino}-4-(4-fluoro-2-methylphenyl)pyridin-2-yl]cyclohex-3-enyl}acetic acid (0.045 g) and 10% palladium on carbon (0.03 g, wet) in methanol (1.5 mL) was stirred at room temperature for 5 hours. To the reaction mixture was added 10% palladium on carbon (0.03 g, wet). Under a hydrogen gas atmosphere, the resulting mixture was stirred at room temperature overnight. The reaction mixture was filtered through a Celite (registered trademark) pad, and the filtrate was concentrated under reduced pressure to give the title compound (0.04 g).

Example 6

{4-[5-{[2-(3,5-Bistrifluoromethylphenyl)-2-methyl-propionyl]methylamino}-4-(4-fluoro-2-methylphenyl)pyridin-2-yl]-1-hydroxycyclohexyl}acetic Acid To a mixture of {4-[5-{[2-(3,5bistrifluoromethylphenyl)-2-methylpropionyl]methylamino}-4-(4-fluoro-2-methylphenyl)pyridin-2-yl]-1-hydroxycyclohexyl}acetic acid ethyl ester (0.05 g), tetrahydrofuran (1.00 mL), methanol (0.50 mL) and water (0.50 mL) was added lithium hydroxide monohydrate (0.015 g) at room temperature, and the mixture was stirred at the same temperature overnight. To the reaction mixture was added 2.0 mol/L hydrochloric acid (0.20 mL), and the solvent was removed under reduced pressure. To the residue was added water, and the resulting mixture was extracted with ethyl acetate. The organic layer was washed with brine, and dried over anhydrous magnesium sulfate. The solvent was concentrated under reduced pressure to give the title compound (0.046 g).

Example 7

6-[5-{[2-(3,5-Bistrifluoromethylphenyl)-2-methyl-propionyl]methylamino}-4-(4-fluoro-2-methylphenyl)pyridin-2-yl]spiro[2.5]octane-1-carboxylic Acid A mixture of 6-[5-{[2-(3,5-bistrifluoromethylphenyl)-2-methylpropionyl]methylamino}-4-(4-fluoro-2-methylphenyl)pyridin-2-yl]spiro[2.5]octane-2-carboxylic acid ethyl ester (0.020 g), 1.0 mol/L aqueous sodium hydroxide solution (0.09 mL), tetrahydrofuran (0.60 mL) and methanol (0.30 mL) was stirred at 140° C. under microwave irradiation for 1 hour and a half. The reaction mixture was cooled to room temperature and water was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate/methanol=40/60/0-0/100/0-0/90/10) to give the title compound (0.005 g).

Example 8

{4-[5-{[2-(3,5-Bistrifluoromethylphenyl)-2-methyl-propionyl]methylamino}-6-cyano-4-(4-fluoro-2-methylphenyl)pyridin-2-yl]cyclohexyl}acetic Acid To a mixture of {4-[5-{[2-(3,5-bistrifluoromethylphenyl)-2-methylpropionyl]methylamino}-6-cyano-4-(4-fluoro-2-methylphenyl)pyridin-2-yl]cyclohexyl}acetic acid methyl ester (0.017 g), tetrahydrofuran (0.30 mL), methanol (0.15 mL) and water (0.15 mL) was added lithium hydroxide monohydrate (0.005 g) at room temperature, and the mixture was stirred at the same temperature for 2 days. The reaction mixture was neutralized by the addition of acetic acid. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=50/50-0/100) to give the title compound (0.008 g).

Example 9

{4-[5-{[2-(3,5-Bistrifluoromethylphenyl)-2-methyl-propionyl]methylamino}-4-ortho-tolylpyridine-yl]-cyclohexyl}acetic Acid To a mixture of {4-[5-{[2-(3,5-bistrifluoromethylphenyl)-2-methylpropionyl]methylamino}-4-ortho-tolylpyridin-2-yl]-cyclohexyl}acetic acid methyl ester (0.08 g), tetrahydrofuran (1.00 mL), methanol (0.50 mL) and water (0.50 mL) was added lithium hydroxide monohydrate (0.021 g) at room temperature, and the mixture was stirred at the same temperature for 3 hours. To the reaction mixture was added 2.0 mol/L hydrochloric acid (0.28 mL), and the solvent was removed under reduced pressure. To the residue was added water, and the resulting mixture was extracted with ethyl acetate. The organic layer was washed with brine, and dried over anhydrous magnesium sulfate. The solvent was concentrated under reduced pressure to give the title compound (0.071 g).

Example 10

2-{4-[5-{[2-(3,5-Bistrifluoromethylphenyl)-2-methylpropionyl]methylamino}-4-(4-fluoro-2-methylphenyl)pyridin-2-yl]cyclohexyl}propionic Acid A mixture of 2-{4-[5-{[2-(3,5-Bistrifluoromethylphenyl)-2-methylpropionyl]methylamino}4-(4-fluoro-2-methylphenyl)pyridin-2-yl]cyclohexyl}propionic acid ethyl ester (0.11 g), 1.0 mol/L aqueous sodium hydroxide solution (0.50 mL), tetrahydrofuran (0.50 mL) and methanol (1.50 mL) was stirred at 140° C. under microwave irradiation for 1 hour and a half. The reaction mixture was cooled to room temperature and 1.0 mol/L hydrochloric acid (0.60 mL) was added. The resulting mixture was extracted with ethyl acetate. The organic layer was washed with water and brine, and dried over anhydrous magnesium sulfate. The solvent was concentrated under reduced pressure to give the title compound (0.10 g).

Example 11 trans-2-{4-[5-{[2-(3,5-Bistrifluoromethylphenyl)-2-methylpropionyl]methylamino}-4-(4-fluoro-2-methylphenyl)pyridin-2-yl]cyclohexyl}-2-methylpropionic Acid A mixture of trans-2-{4-[5-{[2-(3,5-bistrifluoromethylphenyl)-2-methylpropionyl]methylamino}-4-(4-fluoro-2-methylphenyl)-pyridin-2-yl]cyclohexyl}-2-methylpropionic acid ethyl ester (0.054 g), 1.0 mol/L aqueous sodium hydroxide solution (0.25 mL), tetrahydrofuran (0.25 mL) and methanol (0.75 mL) was stirred at 140° C. under microwave irradiation for 1 hour and a half. The reaction mixture was cooled to room temperature and 1.0 mol/L aqueous sodium hydroxide solution (0.25 mL) was added. The resulting mixture was stirred at 140° C. under microwave irradiation for 1 hour and a half. The reaction mixture was cooled to room temperature and 1.0 mol/L hydrochloric acid (0.60 mL) was added. The resulting mixture was extracted with ethyl acetate. The organic layer was washed with water and brine, and dried over anhydrous magnesium sulfate. The solvent was concentrated under reduced pressure to give the title compound (0.022 g).

Example 12 cis-2-{4-[5-{[2-(3,5-Bistrifluoromethylphenyl)-2-methylpropionyl]methylamino}-4-(4-fluoro-2-methylphenyl)pyridin-2-yl]cyclohexyl}-2-methylpropionic Acid A mixture of cis-2-{4-[5-{[2-(3,5-bistrifluoromethylphenyl)-2-methylpropionyl]methylamino}-4-(4-fluoro-2-methylphenyl)pyridin-2-yl]cyclohexyl}-2-methylpropionic acid ethyl ester (0.044 g), 1.0 mol/L aqueous sodium hydroxide solution (0.20 mL), tetrahydrofuran (0.20 mL) and methanol (0.60 mL) was stirred at 140° C. under microwave irradiation for 1 hour and a half. The reaction mixture was cooled to room temperature and 1.0 mol/L aqueous sodium hydroxide solution (0.20 mL) was added. The resulting mixture was stirred at 140° C. under microwave irradiation for 1 hour and a half. The reaction mixture was cooled to room temperature and 1.0 mol/L hydrochloric acid (0.50 mL) was added. The resulting mixture was extracted with ethyl acetate. The organic layer was washed with water and brine, and dried over anhydrous magnesium sulfate, and the solvent was removed under reduced pressure. The obtained crude product was purified by column chromatography on silica gel (eluent: n-hexane/ethyl acetate=90/10-10/90) to give the title compound (0.014 g).

Example 13 and 14 trans-{4-[5-{[2-(3,5-Bistrifluoromethylphenyl)-2-methylpropionyl]methylamino}-4-(4-fluoro-2-methylphenyl)pyridin-2-yl]cyclohexyl}acetic acid (Example 13), and cis-{4-[5-{[2-(3,5-bistrifluoromethylphenyl)-2-methylpropionyl]methylamino}-4-(4-fluoro-2-methylphenyl)pyridin-2-yl]cyclohexyl}acetic acid (Example 14)

(1) Synthesis of a Mixture of Trans and Cis Isomers

To a mixed solution of {4-[5-{[2-(3,5-bistrifluoromethylphenyl)-2-methylpropionyl]methylamino}-4-(4-fluoro-2-methylphenyl)pyridin-2-yl]cyclohexyl}-acetic acid methyl ester (2.13 g) in tetrahydrofuran (32 mL)-methanol (16 mL)-water (16 mL) was added lithium hydroxide monohydrate (0.41 g) at room temperature and the mixture was stirred at the same temperature for 17 hours. To the reaction mixture was added 2.0 mol/L hydrochloric acid (4.9 mL), and the solvent was removed under reduced pressure. To the residue was added water, and the resulting mixture was extracted with ethyl acetate. The organic layer was washed with brine, and dried over anhydrous magnesium sulfate. The solvent was concentrated under reduced pressure to give a crude product (a mixture of trans- and cis-{4-[5-{[2-(3,5-bistrifluoromethylphenyl)-2-methylpropionyl]methylamino}-4-(4-fluoro-2-methylphenyl)pyridin-2-yl]cyclohexyl}acetic acid) (2.08 g).

(2) Separation of trans and cis Isomers

A mixture of trans- and cis-{4-[5-{[2-(3,5-bistrifluoromethylphenyl)-2-methylpropionyl]methylamino}-4-(4-fluoro-2-methylphenyl)pyridin-2-yl]cyclohexyl}acetic acid (36.6 g) was separated by liquid chromatography under the following conditions to give Example 13 (17.0 g) and Example 14 (16.2 g) respectively.

[Separation Conditions of the Liquid Chromatography]
(A) Preparative Isolation System
Device name: K-Prep (KYOTO CHROMATO Co., Ltd.):
(B) Separation Conditions
Column: CHIRALPAK (registered trademark) IA;
Size: 5 cm I.D.×25 cmL.;
Particle size: 5 μm:
Mobile phase: n-hexane/ethanol/acetic acid=85/15/0.1<v/v/v>
Flow rate: 35 mL/min;
Temperature: 30° C.;
Detection wavelength: 254 nm;
Injection method: Loop injection;
Injection volume: 10-20 mL (20 g/L solution)
(C) Retention Time
Example 13: approximately 21 min. Example 14: approximately 17 min
Example 13 and 14 were analyzed under the following analytical conditions.
|Analytical Conditions of the Liquid Chromatography|
(A) Analytical System
Pump: LC-20AD (Shimadzu Corporation);

Detector: SPD-20A (Shimadzu Corporation):
Auto Sampler. SIL-20A (Shimadzu Corporation)
(B) Analytical Conditions
Column: CHIRALPAK (registered trademark) IA;
Size:0.46 cmI.D.×25 cmL.;
Mobile phase: n-hexane/ethanol/acetic acid=85/15/0.1<v/v/v>
Flow rate: 1.0 mL/min;
Temperature: 40° C.;
Detection wavelength: 254 nm;
Injection volume: 10 μL
(C) Retention Time
Example 13: 6.164 min. Example 14: 5.016 min Example 15

{4-[5-{[2-(3,5-Bistrifluoromethylphenyl)-2-methyl-propionyl]methylamino}-4-(4-fluoro-2-methylphenyl)pyridin-2-yl]-1-methylcycloheyl}acetic Acid To a mixture of {4-[5-{[2-(3,5-bistrifluoromethylphenyl)-2-methylpropionyl]methylamino}-4-(4-fluoro-2-methylphenyl)pyridin-2-yl]-1-methylcyclohexyl}acetic acid methyl ester (0.078 g), tetrahydrofuran (0.60 mL), methanol (0.30 mL) and water (0.30 mL) was added lithium hydroxide monohydrate (0.022 g) at room temperature, and the mixture was stirred at the same temperature for 1 hour and at 50° C. for 3 hours. The reaction mixture was neutralized by the addition of acetic acid. The resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane ethyl acetate/methanol=20/80/0-0/100/0-0/90/10) to give the title compound (0.069 g).

Example 16

[4-(5-{[2-(3,5-Bistrifluoromethylphenyl)-2-methyl-propionyl]methylamino}-6-cyano-4-ortho-tolylpyridin-2-yl)cyclohexyl]acetic Acid To a mixture of [4-(5-{[2-(3,5-bistrifluoromethylphenyl)-2-methylpropionyl]methylamino}-6-cyano-4-ortho-tolylpyridin-2-yl)cyclohexyl]acetic acid ethyl ester (0.018 g), tetrahydrofuran (0.40 mL), methanol (0.20 mL) and water (0.20 mL) was added lithium hydroxide monohydrate (0.005 g) at room temperature, and the mixture was stirred at the same temperature overnight. The reaction mixture was neutralized by the addition of acetic acid. The resulting mixture was extracted with ethyl acetate. The organic layer was washed with water and brine, and dried over anhydrous magnesium sulfate. The solvent was concentrated under reduced pressure to give the title compound (0.016 g).

Example 17

{4-[5-{[2-(3,5-Bistrifluoromethylphenyl)-2-methyl-propionyl]methylamino}-6-chloro-4-(4-fluoro-2-methylphenyl)pyridin-2-yl]cyclohexyl}acetic Acid To a mixture of {4-[5-{[2-(3,5-bistrifluoromethylphenyl)-2-methylpropionyl]methylamino}-6-chloro-4-(4-fluoro-2-methylphenyl)pyridin-2-yl]cyclohexyl}acetic acid ethyl ester (0.020 g), tetrahydrofuran (0.50 mL), methanol (0.25 mL) and water (0.25 mL) was added lithium hydroxide monohydrate (0.005 g) at room temperature, and the mixture was stirred at the same temperature for 2 hours. The reaction mixture was neutralized by the addition of acetic acid. The resulting mixture was extracted with ethyl acetate. The organic layer was washed with water and brine, and dried over anhydrous magnesium sulfate. The solvent was concentrated under reduced pressure to give the title compound (0.018 g).

Example 18

{4-[5-{[2-(3,5-Bistrifluoromethylphenyl)-2-methyl-propionyl]methylamino}-4-(4-fluoro-2-methylphenyl)-6-methylpyridin-2-yl]cyclohexyl}acetic Acid To a mixture of {4-[5-{[2-(3,5-bistrifluoromethylphenyl)-2-methylpropionyl]methylamino}-4-(4-fluoro-2-methylphenyl)-6-methylpyridin-2-yl]cyclohexyl}acetic acid ethyl ester (0.019 g), tetrahydrofuran (0.50 mL), methanol (0.25 mL) and water (0.25 mL) was added lithium hydroxide monohydrate (0.005 g) at room temperature, and the mixture was stirred at the same temperature overnight. The reaction mixture was neutralized by the addition of acetic acid. The resulting mixture was extracted with ethyl acetate. The organic layer was washed with water and brine, and dried over anhydrous magnesium sulfate. The solvent was concentrated under reduced pressure to give the title compound (0.018 g).

Example 19

{4-[5-{[2-(3,5-Bistrifluoromethylphenyl)-2-methyl-propionyl]methylamino}-4-(4-fluoro-2-methylphenyl)-6-hydroxymethylpyridin-2-yl]cyclohexyl}acetic Acid To a mixture of a mixture of {4-[5-{[2-(3,5-bistrifluoromethylphenyl)-2-methylpropionyl]methylamino}-4-(4-fluoro-2-methylphenyl)-6-hydroxymethylpyridin-2-yl]cyclohexyl}acetic acid ethyl ester and {4-[5-{[2-(3,5-bistrifluoromethylphenyl)-2-methylpropionyl]methylamino}-4-(4-fluoro-2-methylphenyl)-6-hydroxymethylpyridin-2-yl]cyclohexyl}acetic acid methyl ester (0.025 g), tetrahydrofuran (0.50 mL), methanol (0.25 mL) and water (0.25 mL) was added lithium hydroxide monohydrate (0.007 g) at room temperature, and the mixture was stirred at same temperature overnight. The reaction mixture was neutralized by the addition of acetic acid. The resulting mixture was extracted with ethyl acetate. The organic layer was washed with water and brine, and dried over anhydrous magnesium sulfate. The solvent was concentrated under reduced pressure to give the title compound (0.023 g).

Example 20 and 21 trans-{4-[5-{[2-(3,5-Bistrifluoromethylphenyl)-2-methylpropionyl]methylamino}-6-cyano--4-(4-fluoro-2-methylphenyl)-pyridin-2-yl]cyclohexyl}acetic acid (Example 20) and cis-{4-[5-{[2-(3,5-bistrifluoromethylphenyl)-2-methylpropionyl]methylamino}-6-cyano-4-(4-fluoro-2-methylphenyl)pyridin-2-yl]cyclohexyl}acetic acid (Example 21)

A mixture of trans- and cis-{4-[5-{[2-(3,5-bistrifluoromethylphenyl)-2-methylpropionyl]methylamino}-6-cyano-4-(4-fluoro-2-methylphenyl)pyridin-2-yl]cyclohexyl}acetic acid (Example 8) (0.18 g) was isolated by liquid chromatography under the following conditions to give Example 20 (0.035 g) and Example 21 (0.037 g) respectively.
[Separation Conditions of the Liquid Chromatography]
(A) Preparative Isolation System
Device name: Preparative HPLC System (Gilson, Inc.)
(B) Separation Conditions
Column: InterSustain (registered trademark) CIS;
Size: 20 mmI.D.×50 mmL;
Particle size; 5 μm
Mobile phase: acetonitrile/10 mM aqueous ammonium acetate solution=45/55<v/v>;
Flow rate: 30 mL/min;
Temperature: room temperature;
Detection wavelength: 220 nm
(C) Retention Time
Example 20: approximately 10.4 min, Example 21: approximately 9 min
Example 20 and 21 were analyzed under the following analytical conditions.
[Analytical Conditions of the Liquid Chromatography]
(A) Analytical System
Pump:LC-10AT (Shimadzu Corporation);
Detector: SPD-10A (Shimadzu Corporation);
Auto Sampler: SIL-10A (Shimadzu Corporation)
(B) Analytical Conditions
Column: Inertsil (registered trademark) ODS-3;
Size: 4.6 mmI.D.×250 mmL.;
Mobile phase: acetonitrile/10 mM aqueous ammonium acetate solution=40/60-80/20<v/v>
Flow rate: 1.0 mL/min;
Temperature: 40° C.;
Detection wavelength: 225 nm;
Injection volume: 5 μL
(C) Retention Time
Example 20: 16.786 min. Example 21: 17.286 min Tables 1 to 11 show the chemical structures of the above compounds of Reference Examples 1 to 63, and the chemical structures and the physical properties of the above compounds of Examples 1 to 21. The abbreviations in these Tables: "Ref No.", "Ex No.", "Str.", "Physical data", "¹H-NMR" "DMSO-d6" and "CDCl₃," represent Reference Example number, chemical structure, physical properly, hydrogen nuclear magnetic resonance spectrum, dimethylsulfoxide-d6 and chloroform-d1, respectively. And, "MS" and "ESI_APCI" represent mass spectrometry and measurement of Electrospray ionization-Atmospheric pressure chemical ionization, respectively.

TABLE 1

| Ref. No. | Str. |
|---|---|
| 1 | |
| 2 | |
| 3 | |
| 4 | |
| 5 | |
| 6 | |
| 7 | |
| 8 | |

TABLE 1-continued

| Ref. No. | Str. |
|---|---|
| 9 | [Structure: 6-chloro-4-methylpyridin-3-yl with N(CH3)C(O)OC(CH3)3 (Boc-methylamino)] |
| 10 | [Structure: 6-chloro-4-methyl-N-methylpyridin-3-amine] |
| 11 | [Structure: 6-chloro-4-(4-fluoro-2-methylphenyl)-N-methylpyridin-3-amine] |
| 12 | [Structure: 6-chloro-N-methyl-4-(o-tolyl)pyridin-3-amine] |
| 13 | [Structure: 6-chloro-3-nitropyridine-2-carbonitrile] |
| 14 | [Structure: 3-amino-6-chloropyridine-2-carbonitrile] |

TABLE 2

| Ref. No. | Str. |
|---|---|
| 15 | [Structure: 3-amino-4-bromo-6-chloropyridine-2-carbonitrile] |
| 16 | [Structure: 3-amino-6-chloro-4-(4-fluoro-2-methylphenyl)pyridine-2-carbonitrile] |
| 17 | [Structure: 3-(benzyloxy)-2-(3,5-bis(trifluoromethyl)phenyl)-2-methylpropanoic acid] |

TABLE 2-continued

| Ref. No. | Str. |
|---|---|
| 18 | |
| 19 | |
| 20 | |
| 21 | |

TABLE 2-continued
| Ref. No. | Str. |
|---|---|
| 22 | 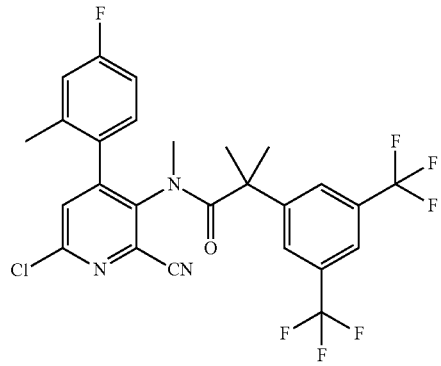 [SMILES: Cc1cc(F)ccc1-c1cc(Cl)nc(C#N)c1N(C)C(=O)C(C)(C)c1cc(C(F)(F)F)cc(C(F)(F)F)c1] |
| 23 | 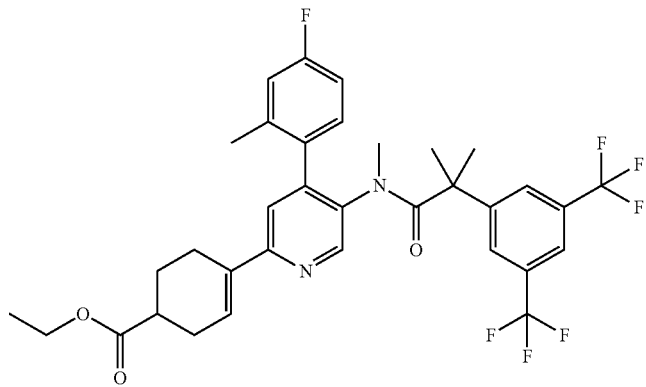 [SMILES: CCOC(=O)C1CC=C(c2cc(-c3ccc(F)cc3C)c(N(C)C(=O)C(C)(C)c3cc(C(F)(F)F)cc(C(F)(F)F)c3)cn2)CC1] |
| 24 | 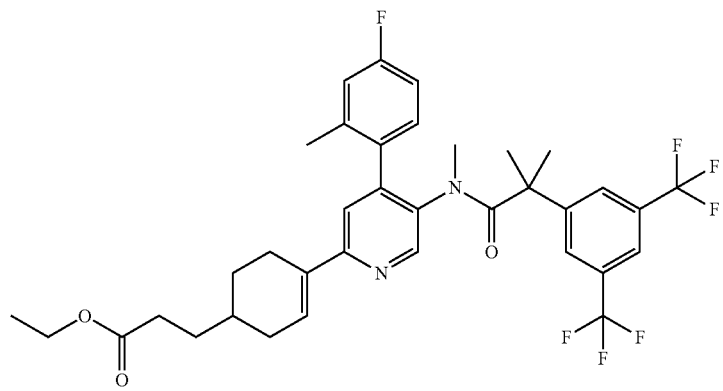 [SMILES: CCOC(=O)CCC1CC=C(c2cc(-c3ccc(F)cc3C)c(N(C)C(=O)C(C)(C)c3cc(C(F)(F)F)cc(C(F)(F)F)c3)cn2)CC1] |

TABLE 3

| Ref. No. | Str. |
|---|---|
| 25 | |
| 26 | |
| 27 | |
| 28 | |

TABLE 3-continued

| Ref. No. | Str. |
|---|---|
| 29 | |
| 30 | |
| 31 | |
| 32 | |

TABLE 3-continued

| Ref. No. | Str. |
|---|---|
| 33 | |
| 34 | |

TABLE 4

| Ref. No. | Str. |
|---|---|
| 35 | |

TABLE 4-continued
| Ref. No. | Str. |
|---|---|
| 36 | 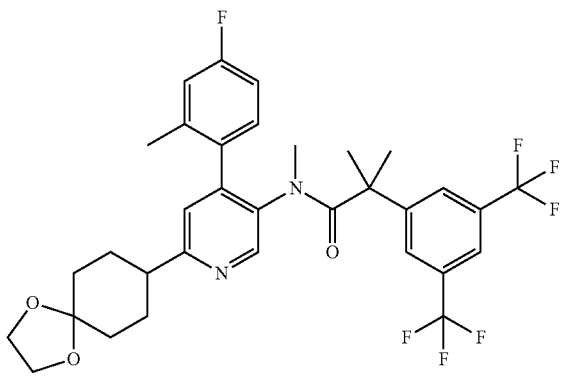 [SMILES: Cc1cc(F)ccc1-c1cc(C2CCC3(CC2)OCCO3)ncc1N(C)C(=O)C(C)(C)c1cc(C(F)(F)F)cc(C(F)(F)F)c1] |
| 37 | 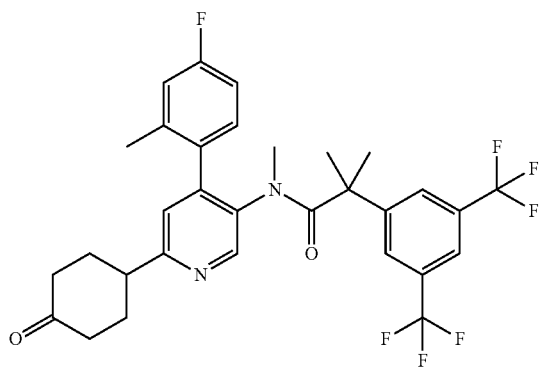 [SMILES: Cc1cc(F)ccc1-c1cc(C2CCC(=O)CC2)ncc1N(C)C(=O)C(C)(C)c1cc(C(F)(F)F)cc(C(F)(F)F)c1] |
| 38 | 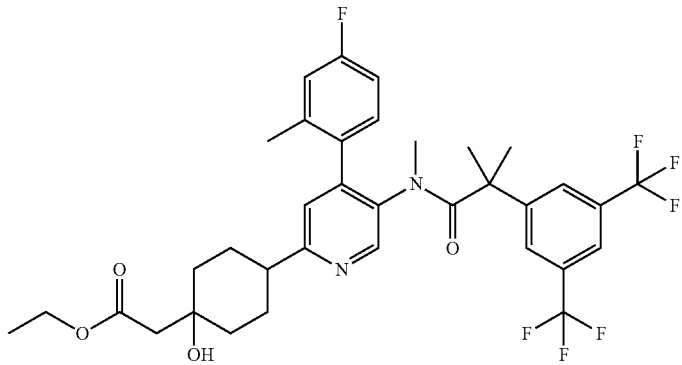 [SMILES: CCOC(=O)CC1(O)CCC(c2cc(-c3ccc(F)cc3C)c(N(C)C(=O)C(C)(C)c3cc(C(F)(F)F)cc(C(F)(F)F)c3)cn2)CC1] |
| 39 | 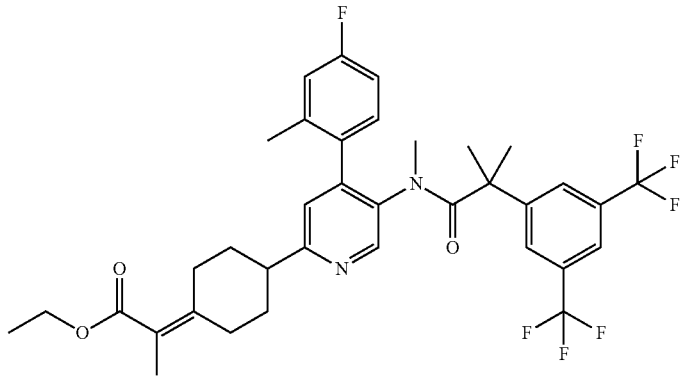 [SMILES: CCOC(=O)C(C)=C1CCC(c2cc(-c3ccc(F)cc3C)c(N(C)C(=O)C(C)(C)c3cc(C(F)(F)F)cc(C(F)(F)F)c3)cn2)CC1] |

TABLE 4-continued
| Ref. No. | Str. |
|---|---|
| 40 | 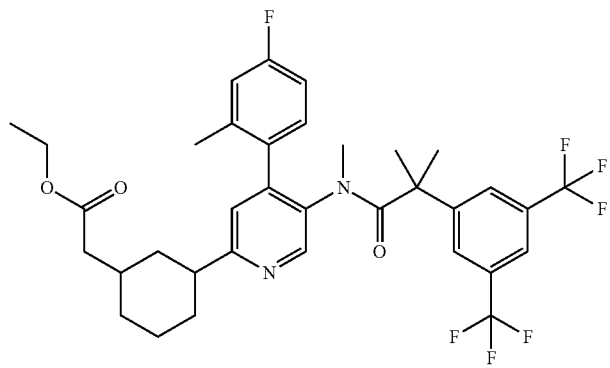 [SMILES: CCOC(=O)CC1CCCC(c2cc(-c3ccc(F)cc3C)c(N(C)C(=O)C(C)(C)c3cc(C(F)(F)F)cc(C(F)(F)F)c3)cn2)C1] |
| 41 | 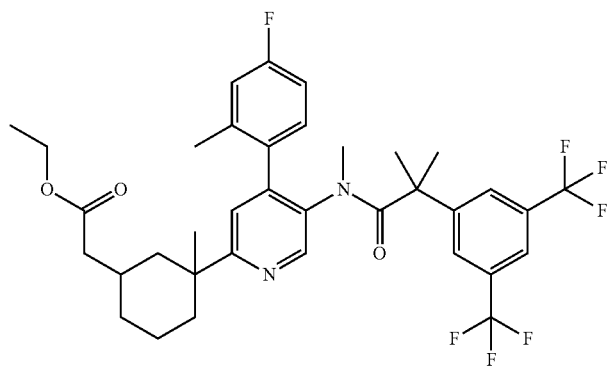 [SMILES: CCOC(=O)CC1CCCC(C)(c2cc(-c3ccc(F)cc3C)c(N(C)C(=O)C(C)(C)c3cc(C(F)(F)F)cc(C(F)(F)F)c3)cn2)C1] |
| 42 | 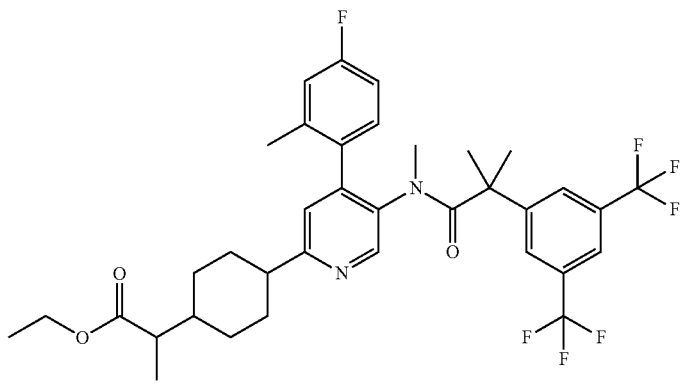 [SMILES: CCOC(=O)C(C)C1CCC(c2cc(-c3ccc(F)cc3C)c(N(C)C(=O)C(C)(C)c3cc(C(F)(F)F)cc(C(F)(F)F)c3)cn2)CC1] |
| 43 | 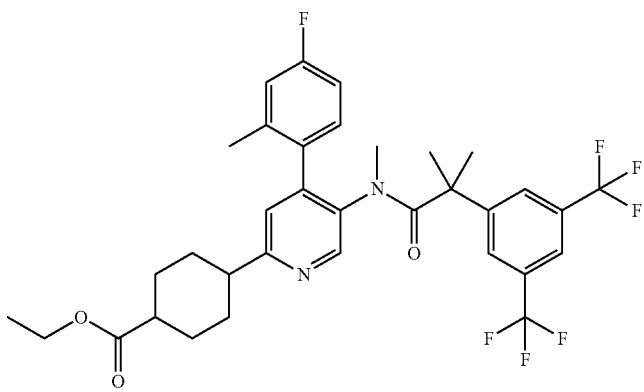 [SMILES: CCOC(=O)C1CCC(c2cc(-c3ccc(F)cc3C)c(N(C)C(=O)C(C)(C)c3cc(C(F)(F)F)cc(C(F)(F)F)c3)cn2)CC1] |

TABLE 4-continued
| Ref. No. | Str. |
|---|---|
| 44 | 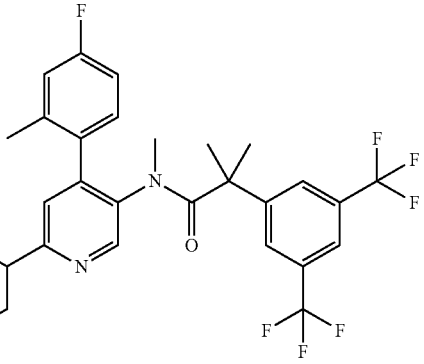 |
TABLE 5
| Ref. No. | Str. |
|---|---|
| 45 | 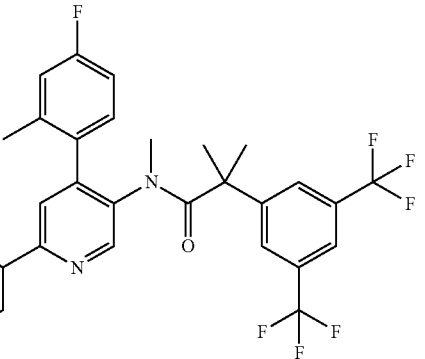 |
| 46 | 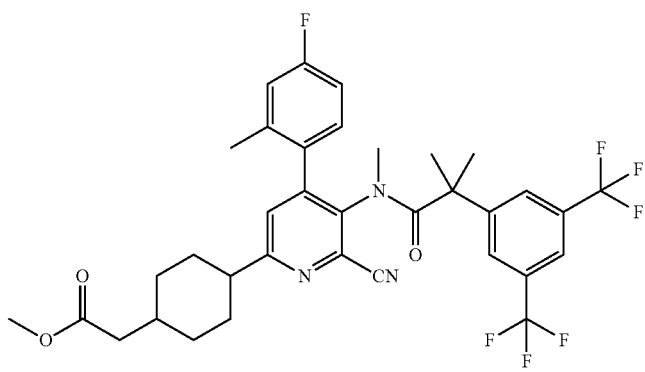 [SMILES: COC(=O)CC1CCC(c2cc(-c3ccc(F)cc3C)c(N(C)C(=O)C(C)(C)c3cc(C(F)(F)F)cc(C(F)(F)F)c3)c(C#N)n2)CC1] |

TABLE 5-continued
| Ref. No. | Str. |
|---|---|
| 47 | 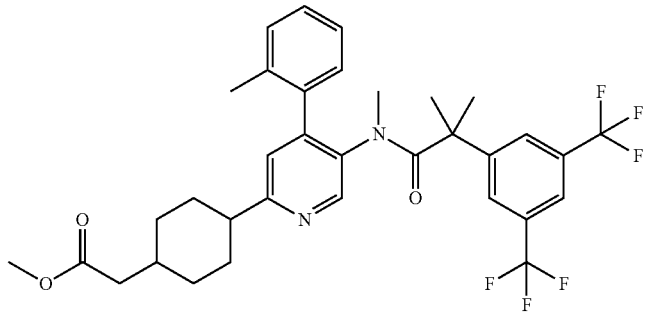 [SMILES: COC(=O)CC1CCC(c2cc(-c3ccccc3C)c(N(C)C(=O)C(C)(C)c3cc(C(F)(F)F)cc(C(F)(F)F)c3)cn2)CC1] |
| 48 | 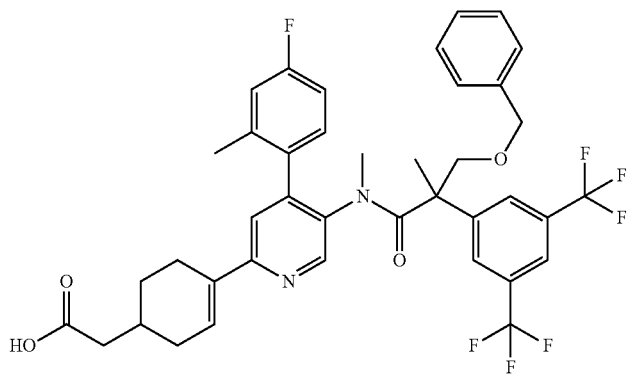 [SMILES: Cc1cc(F)ccc1-c1cc(C2=CCC(CC(=O)O)CC2)ncc1N(C)C(=O)C(C)(COCc1ccccc1)c1cc(C(F)(F)F)cc(C(F)(F)F)c1] |
| 49 | 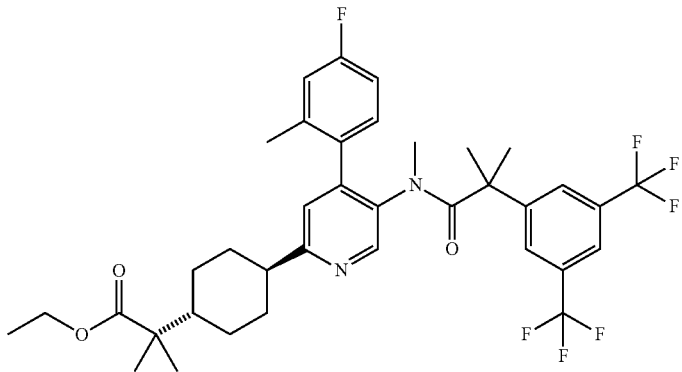 [SMILES: CCOC(=O)C(C)(C)[C@H]1CC[C@H](c2cc(-c3ccc(F)cc3C)c(N(C)C(=O)C(C)(C)c3cc(C(F)(F)F)cc(C(F)(F)F)c3)cn2)CC1] |
| 50 | 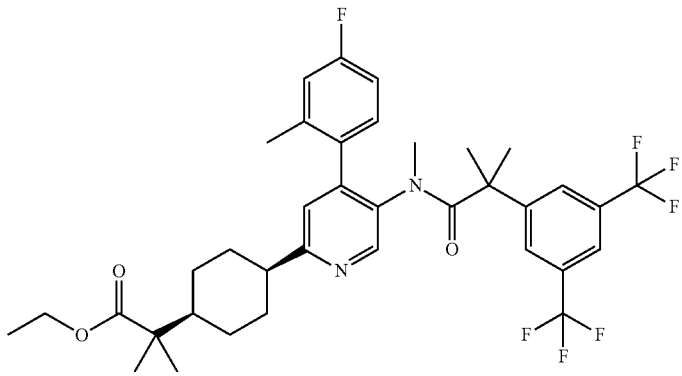 [SMILES: CCOC(=O)C(C)(C)[C@H]1CC[C@@H](c2cc(-c3ccc(F)cc3C)c(N(C)C(=O)C(C)(C)c3cc(C(F)(F)F)cc(C(F)(F)F)c3)cn2)CC1] |

TABLE 5-continued

| Ref. No. | Str. |
|---|---|
| 51 | (structure) |
| 52 | (structure) |

TABLE 6

| Ref. No. | Str. |
|---|---|
| 53 | (structure) |
| 54 | (structure) |

TABLE 6-continued

| Ref. No. | Str. |
|---|---|
| 55 | |
| 56 | |
| 57 | |
| 58 | |

TABLE 6-continued
| Ref. No. | Str. |
|---|---|
| 59 | 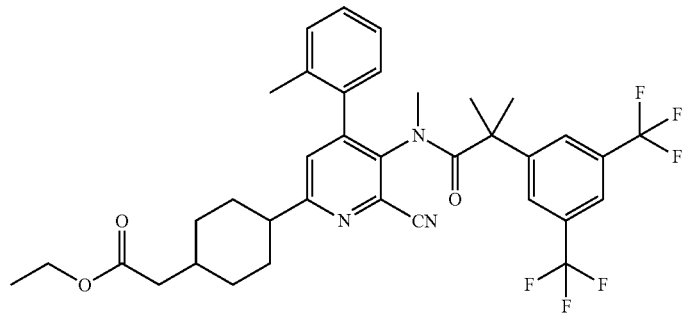 [SMILES: CCOC(=O)CC1CCC(c2cc(-c3ccccc3C)c(N(C)C(=O)C(C)(C)c3cc(C(F)(F)F)cc(C(F)(F)F)c3)c(C#N)n2)CC1] |
| 60 | 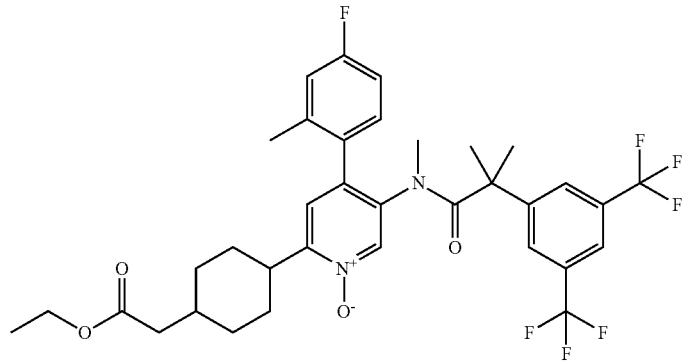 [SMILES: CCOC(=O)CC1CCC(c2cc(-c3ccc(F)cc3C)c(N(C)C(=O)C(C)(C)c3cc(C(F)(F)F)cc(C(F)(F)F)c3)c[n+]2[O-])CC1] |
| 61 | 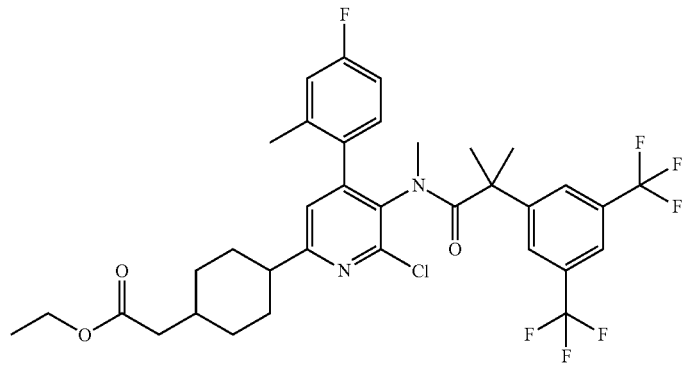 [SMILES: CCOC(=O)CC1CCC(c2cc(-c3ccc(F)cc3C)c(N(C)C(=O)C(C)(C)c3cc(C(F)(F)F)cc(C(F)(F)F)c3)c(Cl)n2)CC1] |
| 62 | 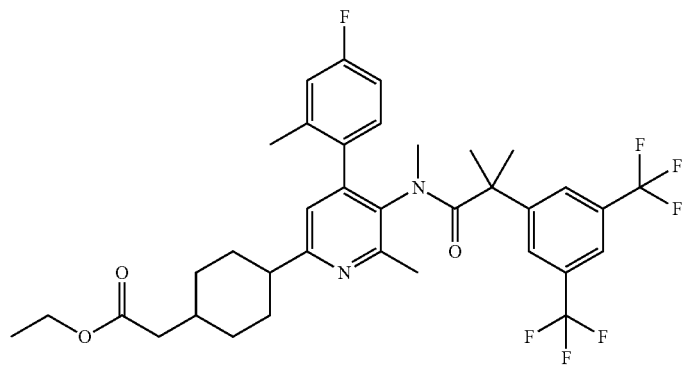 [SMILES: CCOC(=O)CC1CCC(c2cc(-c3ccc(F)cc3C)c(N(C)C(=O)C(C)(C)c3cc(C(F)(F)F)cc(C(F)(F)F)c3)c(C)n2)CC1] |

TABLE 6-continued

| Ref. No. | Str. |
|---|---|
| 63 | (structure) |

20

TABLE 7

| Ex. No. | Str. | Physical data |
|---|---|---|
| 1 | (structure) | ¹H-NMR δ ppm (DMSO-d6): 1.00-3.00 (22H, m), 6.80-7.30 (4H, m), 7.50-7.90 (2H, m), 8.04 (1H, s), 8.30 (1H, s), 12.17 (1H, brs)<br>MS (ESI_APCI, m/z): 625 (M + H)+ |
| 2 | (structure) | ¹H-NMR δ ppm (DMSO-d6): 0.90-2.90 (26H, m), 6.80-7.30 (4H, m), 7.55-7.95 (2H, m), 8.04 (1H, s), 8.20-8.40 (1H, m), 12.03 (1H, brs)<br>MS (ESI_APCI, m/z): 635 (M + H)+ |

TABLE 7-continued
| Ex. No. | Str. | Physical data |
|---|---|---|
| 3 | | $^1$H-NMR δ ppm (CDCl$_3$): 0.80-3.10 (24H, m), 6.75-7.30 (4H, m), 7.65 (2H, brs), 7.77 (1H, brs), 8.37 (1H, brs)<br>MS (ESI_APCI, m/z): 639 (M + H)+ |
| 4 | | $^1$H-NMR δ ppm (CDCl$_3$): 0.80-2.80 (26H, m), 6.80-7.35 (4H, m), 7.67 (2H, brs), 7.78 (1H, brs), 8.39 (1H, brs)<br>MS (ESI_APCI, m/z): 653 (M + H)+ |
| 5 | | $^1$H-NMR δ ppm (DMSO-d6): 1.00-2.90 (21H, m), 3.20-3.90 (2H, m), 4.40-5.00 (1H, m), 6.90-7.35 (4H, m), 7.40-8.15 (3H, m), 8.20-8.45 (1H, m), 12.11 (1H, brs)<br>MS (ESI_APCI, m/z): 655 (M + H)+ |
TABLE 8
| Ex. No. | Str. | Physical data |
|---|---|---|
| 6 |  | $^1$H-NMR δ ppm (DMSO-d6): 1.00-2.90 (24H, m), 6.90-7.35 (4H, m), 7.65-7.85 (2H, m), 8.04 (1H, s), 8.30 (1H, s)<br>MS (ESI_APCI, m/z): 655 (M + H)+ |

TABLE 8-continued
| Ex. No. | Str. | Physical data |
|---|---|---|
| 7 | 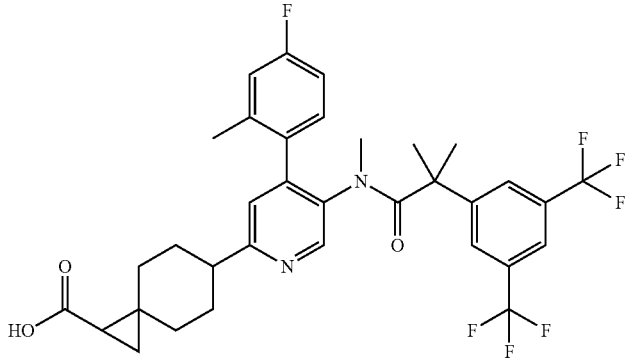 [SMILES: Cc1cc(F)ccc1-c1cc(C2CCC3(CC2)CC3C(=O)O)ncc1N(C)C(=O)C(C)(C)c1cc(C(F)(F)F)cc(C(F)(F)F)c1] | ¹H-NMR δ ppm (CDCl₃): 0.90-2.95 (24H, m), 6.75-7.35 (4H, m), 7.65 (2H, brs), 7.77 (1H, s), 8.30-8.60 (1H, m)<br>MS (ESI_APCI, m/z): 651 (M + H)+ |
| 8 | 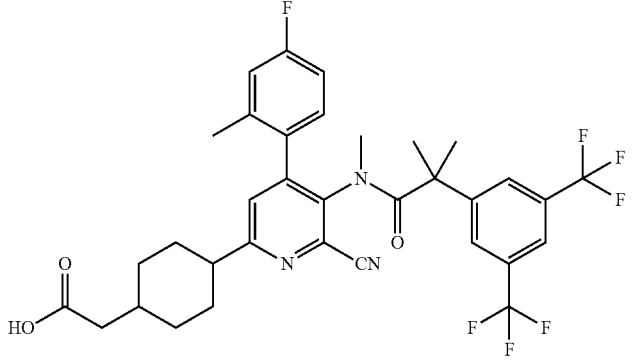 [SMILES: Cc1cc(F)ccc1-c1cc(C2CCC(CC(=O)O)CC2)nc(C#N)c1N(C)C(=O)C(C)(C)c1cc(C(F)(F)F)cc(C(F)(F)F)c1] | ¹H-NMR δ ppm (CDCl₃): 1.05-2.95 (24H, m), 6.80-7.35 (4H, m), 7.50-7.80 (3H, m)<br>MS (ESI_APCI, m/z): 664 (M + H)+ |
| 9 | 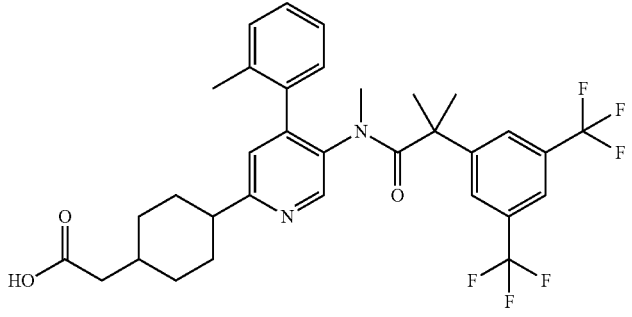 [SMILES: Cc1ccccc1-c1cc(C2CCC(CC(=O)O)CC2)ncc1N(C)C(=O)C(C)(C)c1cc(C(F)(F)F)cc(C(F)(F)F)c1] | ¹H-NMR δ ppm (DMSO-d6): 1.00-2.90 (24H, m), 7.00-7.40 (5H, m), 7.70-7.90 (2H, m), 8.04 (1H, s), 8.25-8.35 (1H, m), 12.00 (1H, brs)<br>MS (ESI_APCI, m/z): 621 (M + H)+ |
| 10 | 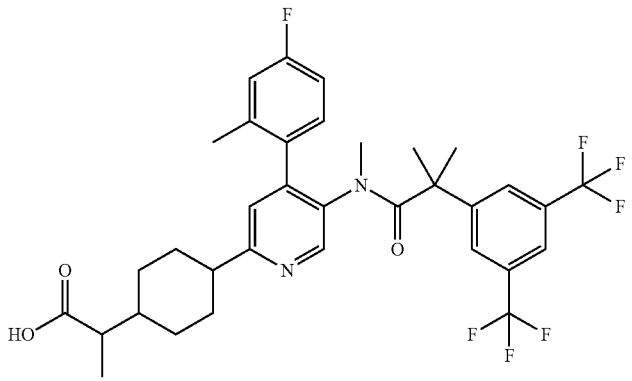 [SMILES: Cc1cc(F)ccc1-c1cc(C2CCC(C(C)C(=O)O)CC2)ncc1N(C)C(=O)C(C)(C)c1cc(C(F)(F)F)cc(C(F)(F)F)c1] | ¹H-NMR δ ppm (DMSO-d6): 1.00-3.00 (26H, m), 6.90-7.30 (4H, m), 7.65-7.85 (2H, m), 8.04 (1H, s), 8.25-8.35 (1H, m), 12.03 (1H, brs)<br>MS (ESI_APCI, m/z): 653 (M + H)+ |

TABLE 9
| Ex. No. | Str. | Physical data |
|---|---|---|
| 11 | 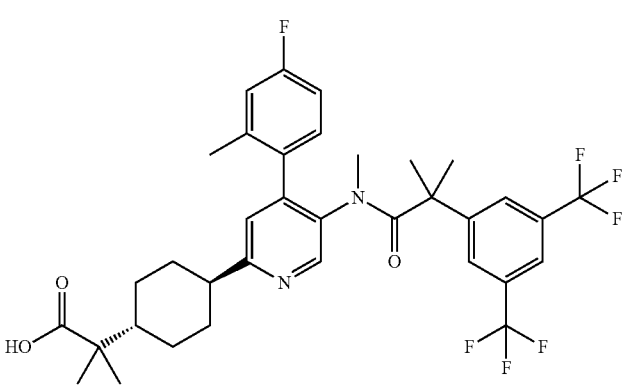 [SMILES: Cc1cc(F)ccc1-c1cc([C@H]2CC[C@H](C(C)(C)C(=O)O)CC2)ncc1N(C)C(=O)C(C)(C)c1cc(C(F)(F)F)cc(C(F)(F)F)c1] | ¹H-NMR δ ppm (DMSO-d6): 1.05 (s, 6H), 1.10-2.80 (22H, m), 6.90-7.30 (4H, m), 7.65-7.85 (2H, m), 8.03 (1H, s), 8.30 (1H, s), 12.07 (1H, brs) MS (ESI_APCI, m/z): 667 (M + H)+ |
| 12 | 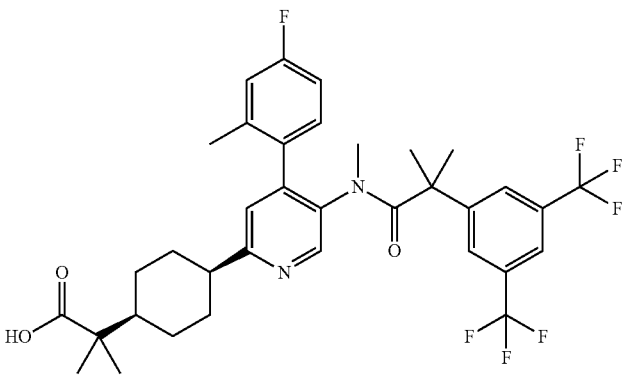 [SMILES: Cc1cc(F)ccc1-c1cc([C@H]2CC[C@@H](C(C)(C)C(=O)O)CC2)ncc1N(C)C(=O)C(C)(C)c1cc(C(F)(F)F)cc(C(F)(F)F)c1] | ¹H-NMR δ ppm (DMSO-d6): 0.95 (s, 6H), 1.00-3.20 (22H, m), 6.90-7.30 (4H, m), 7.65-7.85 (2H, m), 8.04 (1H, s), 8.36 (1H, s), 12.01 (1H, brs) MS (ESI_APCI, m/z): 667 (M + H)+ |
| 13 | 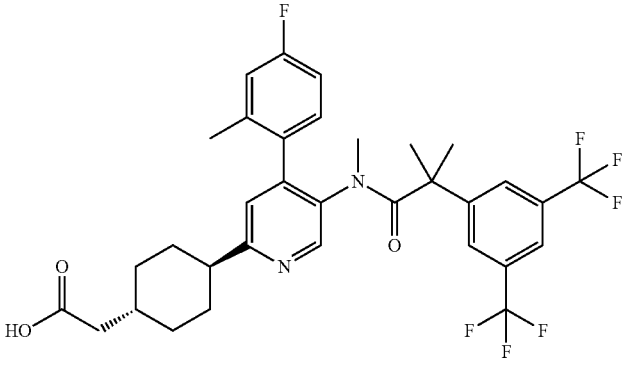 | ¹H-NMR δ ppm (DMSO-d6): 0.90-2.80 (24H, m), 6.80-7.30 (4H, m), 7.60-7.90 (2H, m), 8.04 (1H, s), 8.30 (1H, s), 12.01 (1H, brs) MS (ESI_APCI, m/z): 639 (M + H)+ |
| 14 | 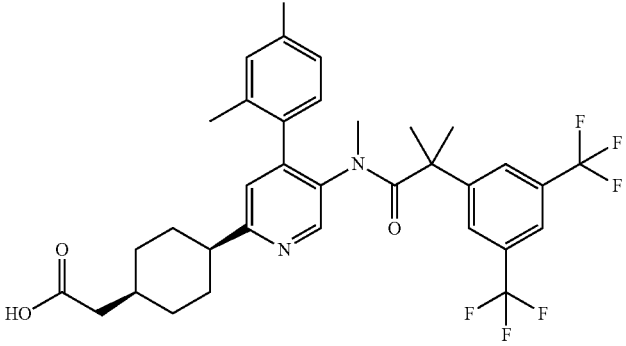 | ¹H-NMR δ ppm (DMSO-d6): 0.90-2.90 (24H, m), 6.80-7.40 (4H, m), 7.60-7.90 (2H, m), 8.04 (1H, s), 8.31 (1H, s), 11.99 (1H, brs) MS (ESI_APCI, m/z): 639 (M + H)+ |

TABLE 9-continued

| Ex. No. | Str. | Physical data |
|---|---|---|
| 15 | | $^1$H-NMR δ ppm (CDCl$_3$): 1.16 (3H, s), 1.20-2.80 (23H, m), 6.80-7.35 (4H, m), 7.66 (2H, brs), 7.78 (1H, s), 8.46 (1H, brs)<br>MS (ESI_APCI, m/z): 653 (M + H)+ |

TABLE 10

| Ex. No. | Str. | Physical data |
|---|---|---|
| 16 | | $^1$H-NMR δ ppm (CDCl$_3$): 0.90-2.95 (24H, m), 6.85-7.40 (4H, m), 7.62 (1H, m), 7.72 (2H, m), 7.75 (1H, brs)<br>MS (ESI_APCI, m/z): 646 (M + H)+ |
| 17 | | $^1$H-NMR δ ppm (CDCl$_3$): 1.05-2.95 (24H, m), 6.80-7.25 (4H, m), 7.68 (1H, m), 7.74 (1H, m), 7.78 (1H, brs)<br>MS (ESI_APCI, m/z): 674 (M + H)+ |
| 18 | | $^1$H-NMR δ ppm (CDCl$_3$): 1.05-2.95 (27H, m), 6.90-7.25 (4H, m), 7.65 (1H, m), 7.69 (1H, m), 7.78 (1H, brs)<br>MS (ESI_APCI, m/z): 653 (M + H)+ |

TABLE 10-continued

| Ex. No. | Str. | Physical data |
|---|---|---|
| 19 | 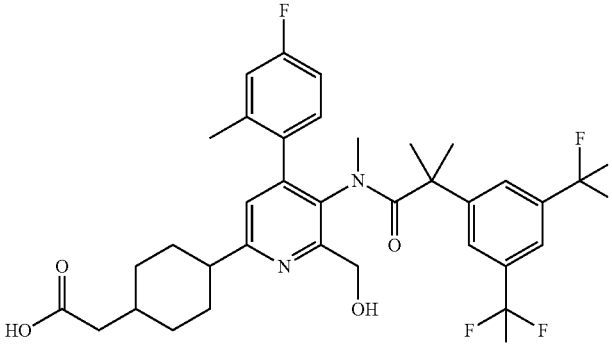 | ¹H-NMR δ ppm (CDCl₃): 1.05-2.95 (25H, m), 4.40-4.50 (1H, m), 4.60-4.75 (1H, m), 6.90-7.25 (4H, m), 7.61 (1H, m), 7.66 (1H, m), 7.79 (1H, brs) MS (ESI_APCI, m/z): 669 (M + H)+ |

TABLE 11

| Ex. No. | Str. | Physical data |
|---|---|---|
| 20 | 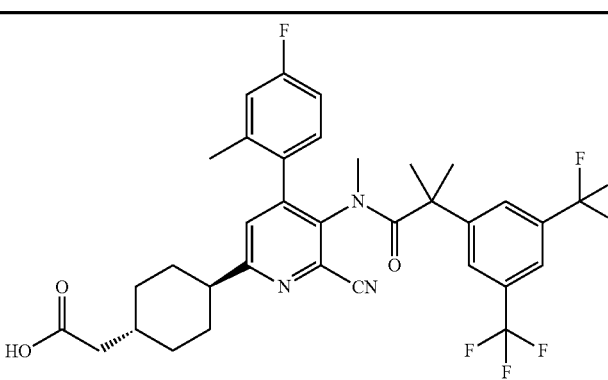 | ¹H-NMR δ ppm (CDCl₃): 1.10-2.90 (24H, m), 6.85-7.25 (4H, m), 7.61 (1H, m), 7.69 (1H, m), 7.77 (1H, brs) MS (ESI_APCI, m/z): 664 (M + H)+ |
| 21 | 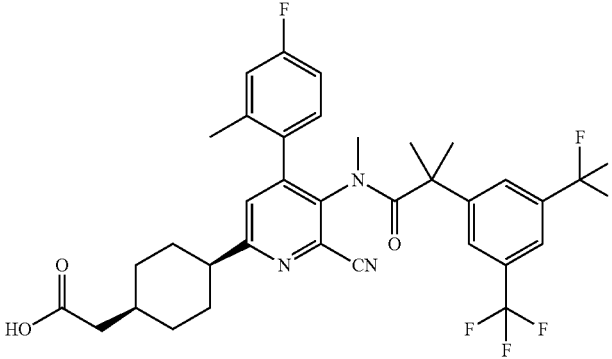 | ¹H-NMR δ ppm (CDCl₃): 1.20-2.95 (24H, m), 6.85-7.25 (4H, m), 7.62 (1H, m), 7.69 (1H, m), 7.77 (1H, brs) MS (ESI_APCI, m/z): 664 (M + H)+ |

Test Example 1

Affinity for Human NK₁ Receptor (1) Preparation of Human NK₁ Receptor Expression Vector PCR was performed using human adult normal tissue-derived brain cDNA (BioChain) as the template, with the forward primer of SEQ ID NO: 1 and the reverse printer of SEQ ID NO:2, using a PCR enzyme, PrimeSTAR Max DNA Polymerase or PrimeSTAR GXL DNA Polymerase (registered trademark, Takara Bio). The amplified product was inserted into a plasmid (pCR-BluntII-TOPO (registered trademark), Life Technologies) using Zero Blunt PGR Cloning Kit (registered trademark, Life Technologies). By a general method, *Escherichia coli* (One Shot TOP 10 competent Cells, Life Technologies) was transformed by the plasmid into which the amplified product had been inserted. The *Escherichia coli* cells were cultured on an LB agar medium containing 50 μg/mL kanamycin for a day. After the culture, a colony was selected and cultured in an LB medium containing 50 μg/mL of kanamycin. After the culture, the plasmid was purified using Quantum Prep Plasmid Miniprep Kit (Bio-Rad). The plasmid was double digested for about two hours using restriction enzymes, XhoI and HindIII (New England Biolabs). Then, electrophoresis using 1% agarose gel was performed, and the fragment that was cleaved was collected and purified using TaKaRa RICO- CHIP (Takara Bio). Separately, a plasmid was also purified from *Escherichia coli* that had been transformed by a vector (pcDNA3.1(−) (registered trademark), Life Technologies), and the plasmid was double digested for about two hours using restriction enzymes, XhoI and HindIII (New England Biolabs). Then, electrophoresis using 1% agarose gel was performed, and the vector that was cleaved was collected and purified using TaKaRa RICOCHLP (Takara Bio). The fragment cut out of pCR-Blunt-II and the pcDNA3.10 vector treated with the restriction enzymes were ligated using DNA Ligation Kit <Mighty Mix> (Takara Bio). By a general method, *Escherichia coli* (One Shot TOP 10 competent cells, Life Technologies) was transformed by the plasmid obtained by the ligation. The *Escherichia coli* cells were cultured on an LB agar medium containing 50 μg/mL of ampicillin for a day. After the culture, a colony was selected and cultured in an LB medium containing 50 μg/mL of ampicillin, and then the plasmid was purified using Quantum Prep Plasmid Miniprep Kit (Bio-Rad). The protein-encoding nucleotide sequence (SEQ ID NO:3) of the obtained plasmid was completely identical to the nucleotide sequence (NM_001058.3) of human tachykinin receptor 1 (TACR1, $NK_1R$) registered on a known database (NCBI). Therefore, it was confirmed that the cloned gene sequence was the nucleotide sequence of human $NK_1$ receptor and that the amino acid sequence which would be translated was human $NK_1$ receptor. The pcDNA3.1(−) (registered trademark) into which the nucleotide sequence of SEQ ID NO:3 was inserted was used as the human $NK_1$ receptor expression plasmid.

(2) Preparation of Human $NK_1$ Receptor-Expressing Cells (2-1) Culture of 293T Cells Using a liquid D-MEM (Dulbecco's Modified Eagle Medium) medium (low glucose, containing L-glutamine, Wako Pure Chemical Industries) supplemented with an antibiotic penicillin-streptomycin solution (Life Technologies, final penicillin concentration of 100 U/mL and final streptomycin concentration of 100 μg/mL) and fetal bovine serum (final concentration of 10%), 293T cells (RIKEN) were cultured in an incubator under the condition of 5% $CO_2$ gas at 37° C.

(2-2) Subculture of 293T Cells

Almost confluent cells were washed with PBS (Phosphate Buffered Saline, Wako Pure Chemical Industries), detached using 0.05% trypsin-EDTA (Life Technologies) and suspended in the liquid medium. The cell suspension was diluted with the above liquid medium in such a manner that the spread ratio became 1:10, and then the cells were cultured.

(2-3) Preparation for Human $NK_1$ Receptor-Expressing Cells

Confluent cells were washed with PBS, detached using 0.05% trypsin-EDTA (Life Technologies) and suspended in a liquid D-MEM medium (low glucose, containing L-glutamine, Wako Pure Chemical Industries) supplemented with fetal bovine serum (final concentration of 10%). The cell suspension was diluted with the liquid medium, and the cells were seeded into the wells of a poly-D-lysine-coated 96-well microplate (BD Biocoat (registered trademark), Nippon Becton Dickinson) at a density of $5 \times 10^4$ cells/well and a liquid medium volume of 100 μL/well. After seeding, the cells were cultured in an incubator under the condition of 5% $CO_2$ gas at 37° C. for about four to five hours, and the cells to be transfected with the human $NK_1$ receptor expression plasmid were thus prepared.

(2-4) Transfection of Human $NK_1$ Receptor Expression Plasmid into 293T Cells

For the transfection of the human $NK_1$ receptor expression plasmid, Lipofectamine 2000 (registered trademark, Life Technologies) was used. The human $NK_1$ receptor expression plasmid was diluted with Opti-MEM (registered trademark) I Reduced-Serum Medium (Life Technologies) to a concentration resulting in 0.2 μg/25 μL/well. At the same time, Lipofectamine 2000 (registered trademark, Life Technologies) was diluted with Opti-MEM (registered trademark) I Reduced-Serum Medium (Life Technologies) to a concentration resulting in 0.4 μL/25 μL/well and incubated at room temperature for five minutes. After five minutes, to form a complex of human $NK_1$ receptor expression plasmid/Lipofectamine 2000, the diluted human $NK_1$ receptor expression plasmid and the diluted Lipofectamine 2000 were mixed and incubated at room temperature for 20 to 25 minutes. After the incubation, 50 μL/well of the complex solution was added to the cells to be transfected with the human $NK_1$ receptor expression plasmid, and the cells were cultured in an incubator under the condition of 5% $CO_2$ gas at 37° C. for about 48 hours. The cells that were cultured for 48 hours were used for the assays as the human $NK_1$ receptor-expressing cells.

(3) Measurement of Binding Affinity to Human $NK_1$ Receptor (3-1) Preparation of Membrane Fraction from Human $NK_1$ Receptor-Expressing Cells Human $NK_1$ receptor-expressing cells were prepared in a 175 $cm^2$ culture flask (Nippon Becton Dickinson). The formation of a complex of the human $NK_1$ receptor expression plasmid and Lipofectamine 2000 was performed by calculating the culture area ratio and increasing the scale of the method described in the above 2-4 by the ratio. The human $NK_1$ receptor-expressing cells were collected in a buffer solution for the membrane fraction preparation (50 mM Tris (Wako Pure Chemical), 120 mM sodium chloride (Wako Pure Chemical Industries), 5 mM potassium chloride (Wako Pure Chemical Industries), 1 mM ethylenediaminetetraacetic acid (Sigma), 0.002 mg/mL chymostatin (Peptide Institute), 0.04 mg/bacitracin (Wako Pure Chemical Industries), 0.005 mg/mL phosphoramidon (Peptide Institute) and 0.5 mM phenylmethylsulfonyl fluoride (Wako Pure Chemical Industries), pH7.4) and centrifuged at 1,880 g for 10 minutes, and the cell sediment was suspended in the buffer solution for the membrane fraction preparation. After freezing and thawing the cells once, the cells were homogenized using a Dounce-type homogenizer (cooled on ice, 1000 rpm, 20 times) The homogenized cell suspension was centrifuged at 20,000 rpm for 10 minutes, and the supernatant was removed to obtain cell sediment. The cell sediment was suspended again in the buffer solution for the membrane fraction preparation and homogenized using a Dounce-type homogenizer (cooled on ice, 1000 rpm, 30 times). The cell suspension was centrifuged at 20,000 rpm for 10 minutes, and the supernatant was removed to obtain cell sediment. The same homogenization and centrifugation were repeated again, and final cell sediment was obtained. The final cell sediment was suspended in a buffer solution for the receptor binding test (50 mM Tris (Wako Pure Chemical Industries). 3 mM manganese chloride (Wako Pure Chemical Industries), 0.002 mg/mL chymostatin (Peptide Institute), 0.04 mg/bacitracin (Wako Pure Chemical Industries) and 0.02% bovine serum albumin (Sigma), pH 7.4), and the protein concentration was measured using BCA Protein Assay Kit (Pierce).

(3-2) Receptor Binding Test

The buffer solution for the receptor binding test was dispensed to the wells of a 96-well assay plate (Greiner) at 22.5 μL/well. DMSO solutions of a test compound, which were prepared at an 80-time higher concentration using 100% dimethyl sulfoxide (DMSO), were added to the wells at 2.5 μL/well (final concentrations of 1 nM to 100 nM), and the solutions were mixed. As a radiolabeled ligand, $^{125}$I-substance P (Substance P, [$^{125}$I]Tyr$^{8}$-, Perkin Elmer) was used. $^{125}$I-substance P was diluted with the buffer solution for the receptor binding test to a concentration resulting in 125 pmol/25 μL/well and added to the 96-well assay plate, and the solutions were mixed. The membrane fraction prepared from the human $NK_1$ receptor-expressing cells was diluted with the buffer solution for the receptor binding test to a concentration resulting in 8 to 10 μg/well, suspended until the suspension became in such a homogenous state that the suspension could flow through a 27G injection needle smoothly and then added to the 96-well assay plate at 150 μL/well. Then, the plate was incubated at room temperature for 60 minutes while shaking the plate. The reaction solutions were suction-filtered through a multiscreen 96-well filter plate (Millipore) which had been pre-treated with 0.3% polyethyleneimine, and the reaction was terminated by washing with a washing solution (50 mM Tris and 0.02% bovine serum albumin, pH 7.4) four times. The bottom of the microplate was dried at 60° C., and then 100 μL/well of MicroScint 20 (PerkinElmer) was dispensed to the wells. The top of the plate was sealed with TopSeal A (PerkinElmer), and the plate was shaken for 5 to 10 minutes. Then, the radioactivities were measured with TopCount NXT (registered trademark) (PerkinElmer). The radioactivity of each well was calculated by subtracting the radioactivity of the well to which 10 μM aprepitant was added (non-specific binding). The binding rate (%) of $^{125}$I-substance P=(the radioactivity of the group to which the test compound was added)/(the radioactivity of the group to which the vehicle was added) ×100 was calculated. Using analysis software, GraphPad Prism (GraphPad Software), the binding rate (%) was plotted against the concentration of the test compound and linearly approximated, and the concentration required for 50% inhibition, $IC_{50}$, was calculated. These results were shown in Table 12 and 13. In the table. Ex. No. means the Example number, and $IC_{50}$ (nM) is the concentration required for 50% inhibition.

(4) Results

TABLE 12

| Ex. No. | $IC_{50}$ (nM) |
| --- | --- |
| 1 | 1.45 |
| 2 | 1.78 |
| 3 | 2.10 |
| 4 | 2.35 |
| 5 | 0.98 |
| 6 | 1.00 |
| 7 | 1.63 |
| 8 | 4.01 |
| 9 | 2.35 |
| 10 | 2.79 |
| 11 | 6.75 |
| 12 | 4.46 |
| 13 | 1.62 |
| 14 | 2.21 |

TABLE 13

| Ex. No. | $IC_{50}$ (nM) |
| --- | --- |
| 16 | 2.78 |
| 17 | 5.51 |
| 18 | 6.45 |
| 19 | 4.96 |
| 20 | 3.27 |
| 21 | 2.36 |

As shown in Table 12 and 13, it was demonstrated that the compounds of the present invention exhibit a high binding affinity for human $NK_1$ receptor.

Test Example 2

Inhibitory Effect on Human $NK_1$ Receptor
(1) Preparation of Human $NK_1$ Receptor-Expressing Cells Human $NK_1$ receptor-expressing cells were prepared by the same methods as those described in 2-3 of Test Example 1.

(2) Study on Inhibitory Effect on Increase in Intracellular Calcium Concentration The human $NK_1$ receptor-expressing cells were washed with 300 μL/well of a washing solution (20 mM HEPES/Hank's Balanced Salt Solution (HBSS) pH 7.3). A fluorescent calcium indicator (Fluo-4 Direct Calcium Assay Kit, Life Technologies, containing 0.42 mM probenecid and 0.1% bovine serum albumin, prepared according to the protocol of the product) was added to the wells at 150 μL/well, and the plate was incubated at 37° C. for 30 minutes in an incubator. Then. DMSO solutions of a test compound, which were prepared at an 80-time higher concentration using 100% dimethyl sulfoxide (DMSO), were added to the wells at 2.5 μL/well (final concentrations of 0.1, 1 and 10 μM), and the solutions were mixed. Then, the plate was further incubated at 3° C. for 30 minutes in an incubator. After 30 minutes, the intracellular calcium concentrations were measured immediately.

The intracellular calcium concentrations were each measured as a fluorescent signal using FDSS (registered trademark) 7000 (Hamamatsu Photonics). A substance P (Peptide Institute. Inc.) solution which was prepared at 0.4 μM or 4 μM using an assay buffer (20 mM HEPES/Hank's Balanced Salt Solution (HBSS) pH 7.3, containing 0.1% bovine serum albumin) was added automatically to each well at 50 μL/well (final concentration of 0.1 or 1 μM) 10 seconds after starting reading, and the fluorescent signal was measured up to 120 seconds.

The intracellular calcium concentration (%) of the cells to which a test compound was added was calculated by the equation below, where the fluorescent signal of the group to which the vehicle (DMSO) was added was regarded as 100%, and the fluorescent signal before the addition of substance P was regarded as 0%. Intracellular calcium concentration (%)=(Fluorescent signal of test compound addition group)/(Fluorescent signal of vehicle addition group)×100

The intracellular calcium concentration (%) calculated was regarded as the remaining agonist activity of substance P (Substance P-Response Remaining: SPRR). These results were shown in Table 14 and 15. In the table, Ex. No. means the Example number. SPRR (%) is the value obtained when the concentration of substance P was 1 μM and the concentration of the compound was 0.1 μM.

(3) Results

TABLE 14

| Ex. No. | SPRR (%) |
|---|---|
| 1 | 20 |
| 2 | 7.5 |
| 3 | 36 |
| 4 | 57 |
| 5 | 26 |
| 6 | 21 |
| 7 | 9.4 |
| 8 | 31 |
| 9 | 42 |
| 10 | 8.6 |
| 11 | 5.4 |
| 12 | 53 |
| 13 | 5.1 |
| 14 | 22 |
| 15 | 3.7 |

TABLE 15

| Ex. No. | SPRR (%) |
|---|---|
| 16 | 37 |
| 19 | 26 |
| 20 | 2.8 |
| 21 | 36 |

As shown in Table 14 and 15, it was demonstrated that the compounds of the present invention exhibit a potent human $NK_1$ receptor antagonist activity.

Test Example 3

Inhibitory Effect on CYP3A4

A dimethyl sulfoxide (DMSO) solution of a test compound with a concentration 1000 times higher than the evaluation concentration was prepared, and a reaction solution was prepared by diluting the solution. Enzyme reaction was performed by incubating in a potassium phosphate buffer solution (pH 7.4) containing 1 nM to 20 µM test compound, 3.2 mM magnesium chloride, 0.2 pmol human CYP3A4 (BD Biosciences), 0.5 mM reduced nicotinamide adenine dinucleotide phosphate (NADPH) and 3 µM Luciferin-IPA (Promega) at 37° C. for 10 minutes. The volume of the reaction solution was 50 µL/well. The 30-minute pre-incubation group was incubated at 37° C. for 30 minutes before adding tire substrate, the Luciferin-IPA solution (12.5 µL/well). At the end of the enzyme reaction, 50 µL/well of a Luciferin detection reagent (Promega) was added to the wells, and the plate was left at room temperature for 20 minutes. Then, the emission intensities were measured with Infinite M1000 (TECAN). The enzyme activities (%) relative to the value of the group to which the test compound was not added were calculated. A dose-response curve was drawn using analysis software, GraphPad Prism (GraphPad Software), and the concentration of each compound that exhibited 50% inhibition, $IC_{50}$, was calculated. As a comparative example, aprepitant, which is an $NK_1$ receptor antagonist, was tested in the same manner.

$IC_{50}$ values of the 30-minute pre-incubation groups using (the test compounds were measured by the above measurement method, and the results are shown in Table 16 and 17. In the table, Ex. No. means the Example number, and $IC_{50}$ (µM) is the concentration required for 50% inhibition.

TABLE 16

| Ex. No. | $IC_{50}$ (µM) |
|---|---|
| 1 | 13 |
| 2 | 6.8 |
| 3 | 9.4 |
| 4 | 7.1 |
| 5 | 13 |
| 6 | 6.1 |
| 7 | 11 |
| 8 | 6.1 |
| 9 | 6.9 |
| 10 | 11 |
| 11 | 2.7 |
| 12 | 2.2 |
| 13 | 8.2 |
| 14 | 7.5 |
| Aprepitant | 0.02 |

TABLE 17

| Ex. No. | $IC_{50}$ (µM) |
|---|---|
| 16 | 3.1 |
| 17 | 3.3 |
| 18 | 4.9 |
| 20 | 5.5 |
| 21 | 4.2 |

As shown in Table 16 and 17, it was demonstrated that the CYP3A4-inhibitory activities of the compounds of the present invention are reduced as compared to that of aprepitant Therefore, it is expected that the compounds of the present invention have fewer drug-drug interactions based on the inhibitory effect on CYP3A4 than aprepitant.

Test Example 4

Effect on Foot-Tapping
(1) Effect on Foot-Tapping

The test compound solution was prepared by dissolving the test compound in a vehicle (a mixture of 50% N,N-dimethylacetamide (Wako Pure Chemical Industries), 30% propylene glycol (Wako Pure Chemical Industries). 4% 2-hydroxypropyl-β-cyclodextrin (Wako Pure Chemical Industries) and 16% distilled water).

A male gerbil (Japan SLC) was anesthetized with isoflurane, and 0.1 mg/kg of a test compound was administered from the jugular vein. After four hours. GR73632 (5 pmol/5 µl saline), which is an $NK_1$ receptor agonist, was administered into the cerebral ventricle at the part 1 mm lateral to and 4.5 mm below the bregma in the head, under anesthesia with isoflurane. After the administration, the gerbil was moved to an observation cage, and the foot-tapping period during 30 minutes after the recovery of the righting reflex was measured. The foot-tapping inhibition rate (%) of each test compound was calculated by the following equation.

Foot-tapping inhibition rate (%)={1−(Fool-tapping period when test compound was administered)/ (Foot-tapping period when solvent was administered)}×100

(2) Measurement of Drug Concentrations

After foot-tapping was finished, laparotomy was performed immediately under anesthesia with ether, and a blood sample was taken from the abdominal vena cava. At the same lime, the brain was extracted. Through a quantitative analysis using liquid chromatography-mass spectrometry (LC/MS), the concentrations of the test compound in the plasma and the brain were measured.

(3) Results

The effects on foot-tapping were measured by the above test method, and the results are shown in Table 18 and 19. In the table, Ex. No. means the Example number. Inhibition (%) is the loot-tapping inhibition rate, and Conc. (nM) is the drug concentration in the brain.

TABLE 18

| Ex. No. | Inhibition (%) | Conc. (nM) |
| --- | --- | --- |
| 1 | 98 | 24 |
| 2 | 100 | 19 |
| 3 | 100 | 48 |
| 4 | 77 | 35 |
| 7 | 90 | 24 |
| 8 | 100 | 59 |
| 9 | 75 | 47 |
| 10 | 97 | 42 |
| 11 | 95 | 72 |
| 13 | 100 | 51 |
| 14 | 99 | 40 |
| 15 | 100 | 39 |

TABLE 19

| Ex. No. | Inhibition (%) | Conc. (nM) |
| --- | --- | --- |
| 16 | 93 | 64 |
| 17 | 96 | 57 |
| 18 | 100 | 47 |
| 19 | 95 | 24 |
| 20 | 100 | 92 |
| 21 | 100 | 92 |

As shown in Table 18 and 19, the compounds of the present invention were penetrated into the central nervous system and exhibited an excellent $NK_1$ receptor antagonist activity also in vivo.

Test Example 5

Ferret Pharmacokinetic Test
(1) Methods

The test compound solution for intravenous administration was prepared by dissolving the test compound in a vehicle (a mixture of 50% N,N-dimethylacetamide (Wako Pure Chemical Industries), 30% propylene glycol (Wako Pure Chemical Industries), 4% 2-hydroxypropyl-β-cyclodextrin (Wako Pure Chemical Industries) and 16% distilled water). As an oral administration solution, the suspension (0.5% methylcellulose) was used.

Under anesthesia with isoflurane, 0.1 mg/kg of the test compound was intravenously administered to a male ferret (Marshall BioResources Japan) from the femoral vein. In the case of oral administration, 1 mg/kg of the test compound was orally administered to an awake animal. After the administration of the test compound, blood samples were taken sequentially from the brachial cephalic vein up to 7 days after the administration. Through a quantitative analysis using liquid chromatography-mass spectrometry (LC/MS), the concentrations of the test compound in the plasma were measured.

(2) Results

The pharmacokinetic test in a ferret was tested by the above test method, and the results are shown in Table 20 and Table 21. In the tables, Ex. No. is the Example number, $t_{1/2}$, CLtot and Vss are the half-life, the total body clearance and the steady-state volume of distribution, based on the plasma concentrations in the case of intravenous administration, respectively. $C_{max}$, AUC and BA are the maximum plasma test compound concentration, the area under the plasma test compound concentration-time curve within 7 days after the administration and the bioavailability, in the case of oral administration, respectively.

TABLE 20

| Ex. No. | $t_{1/2}$ (min) | CLtot (mL/min/kg) | Vss (mL/kg) |
| --- | --- | --- | --- |
| 13 | 2,489 | 0.13 | 401 |

TABLE 21

| Ex. No. | Cmax (ng/mL) | AUC (ng · min/mL) | BA (%) |
| --- | --- | --- | --- |
| 13 | 1,258 | 5,294,066 | 66 |

As shown in Table 20 and Table 21, the compound of the present invention exhibited an excellent oral absorbability with low clearance.

Test Example 6

Effect on Cisplatin-Induced Acute and Delayed Emetic Response
(1) Methods

The test compound solution was prepared by dissolving the test compound in a vehicle (a mixture of 50% N,N-dimetlylacetamide (Wako Pure Chemical Industries). 30% propylene glycol (Wako Pure Chemical Industries), 4% 2-hydroxypropy-β-cyclodextrin (Wako Pure Chemical Industries) and 16% distilled water). The vehicle only was administered to the control group.

Under anesthesia with isoflurane, 0.01 mg/kg or 0.1 mg/kg of the test compound was intravenously administered to a male ferret (Marshall BioResources Japan) from the jugular vein. Cisplatin in saline, which was heated to 40-50° C., was intraperitoneally administered at 5 mg/kg one hour after the drug administration. The ferret was observed for 72 hours from immediately after the cisplatin administration, and the number of retching (periodic abdominal contraction without vomiting of the gastric content) and vomiting was counted.

(2) Results

The results are shown in FIG. 1. In the control group, an increase in the number of retching and vomiting was observed in the acute phase (up to 24 hours after the cisplatin administration) and in the delayed phase (24 hours to 72 hours after the cisplatin administration). In the group to which the compound of Example 13 was intravenously administered, the inhibition of the number of retching and vomiting was observed in the acute phase and in the delayed phase.

It was demonstrated that the compound of the present invention has a long-acting medicinal effect and an inhibitory effect on the cisplatin-induced acute and delayed emetic responses.

Test Example 7

Evaluation of hERG Current
(1) Methods

A dimethyl sulfoxide (DMSO) solution of the test compound with a concentration 1000 times higher than the evaluation concentration (10 μM) was prepared, and a solution with a final application concentration was prepared by diluting the solution. The hERG current was measured by a whole-cell method using a patch clamp system, where a cover glass on which hERG channel-expressing human embryonic kidney (HEK) 293 cells were seeded was placed on a perfusion bath and a perfusion solution was caused to flow. The change in the hERG channel-derived current caused by a pulse protocol (holding potential of −80 mV, depolarization pulse of +20 mV for 1.9 seconds, repolarization pulse of −50 mV for 2 seconds, stimulated at intervals of 15 seconds) of data acquisition/analysis software, pCLAMP9 (Axon instruments. Inc.) was measured. The measurement conditions were a flow rate of about 1.5 mL/min and a temperature of about 33° C. Two wave forms immediately before applying the test compound and two wave forms immediately after the application for 10 minutes were analyzed, and the statistical analysis was performed. The value before the application of the test compound was regarded as 100%, and the change rate based on the value was determined.

(2) Results

The effect of tire test compound on hERG current was evaluated by the above method (the result is shown in Table 22). In the table, Ex. No. means the Example number, and the change rate is the average±the standard error.

TABLE 22

| Ex. No. | % (n = 3) |
|---------|-----------|
| 13 | 81.1 ± 5.6 |
| 14 | 80.3 ± 3.9 |

The compound of the present invention did not cause any change in the hERG current with a statistical significance compared to the vehicle control (0.1% DMSO).

INDUSTRIAL APPLICABILITY

The compounds of the present invention or pharmaceutically acceptable salts thereof have an excellent $NK_1$ receptor antagonist activity, and thus are also useful as an agent for the prevention or treatment of cancer-chemotherapy-induced nausea and vomiting.

SEQUENCE LISTING FREE TEXT

<Sequence Listing 1>
SEQ ID NO: 1 is the sequence of forward primer which was used for DNA amplification of SEQ ID NO:3.
<Sequence listing 2>
SEQ ID NO:2 is the sequence of reverse primer which was used for DNA amplification of SEQ ID NO:3.

The invention claimed is:

1. A method for the suppression or treatment of a disease mediated by NK1 receptor in a subject, said method comprising administering to said subject a therapeutically effective amount of a compound represented by the formula (I):

[Chem. 1]

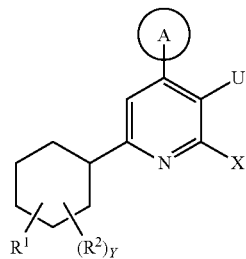

(I)

wherein ring A is a group represented by the following formula:

[Chem. 2]

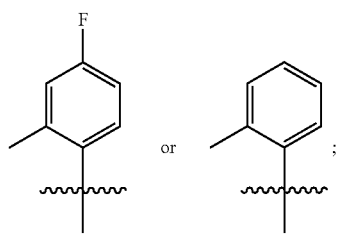

X is a hydrogen atom, cyano, halogen, $C_{1-6}$ alkyl or hydroxymethyl;

$R^1$ is a group represented by the following formula:

[Chem. 3]

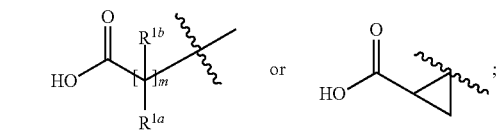

wherein $R^{1a}$ and $R^{1b}$ are each independently any one of a hydrogen atom, a fluorine atom or $C_{1-6}$ alkyl;

m is 0, 1 or 2;

when m is 2, these $R^{1a}$ and $R^{1b}$ are optionally different from each other;

$R^2$ is $C_{1-6}$ alkyl, a hydroxy group or $C_{1-6}$ alkoxy;

U is a group represented by the following formula:

[Chem. 4]

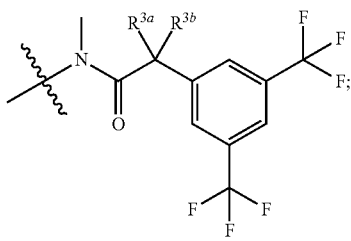

wherein $R^{3a}$ and $R^{3b}$ are each independently a hydrogen atom, $C_{1-6}$ alkyl, hydroxy $C_{1-6}$ alkyl or $C_{1-6}$ alkoxy $C_{1-6}$ alkyl;

Y is 0, 1 or 2;

when Y is 2, two $R^2$ are optionally different from each other;

or a pharmaceutically acceptable salt thereof, and wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus, pain, migraine, tinnitus, benign prostatic hyperplasia, overactive bladder and urinary incontinence.

2. A method for the suppression or treatment of a disease mediated by NK1 receptor in a subject according to claim 1 wherein the compound is represented by the formula (Ia):

[Chem.5]

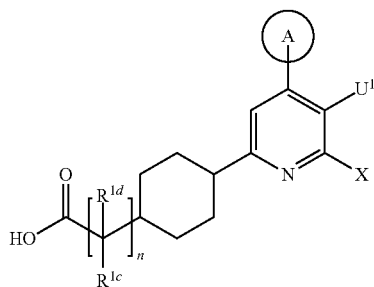

(Ia)

wherein ring A is a group represented by the formula [Chem. 2];

X is a hydrogen atom, cyano, halogen, $C_{1-6}$ alkyl or hydroxymethyl;

$R^{1c}$ and $R^{1d}$ are each independently a hydrogen atom or methyl;

$U^1$ is a group represented by the following formula:

[Chem.6]

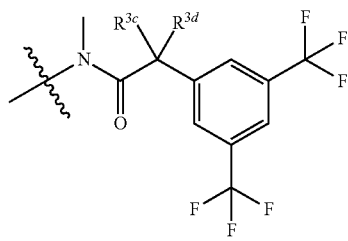

in which $R^{3c}$ and $R^{3d}$ are each independently a hydrogen atom, methyl or hydroxymethyl;

n is 0, 1 or 2;

when n is 2, these $R^{1c}$ and $R^{1d}$ are optionally different from each other;

or a pharmaceutically acceptable salt thereof.

3. A method for the suppression or treatment of a disease mediated by NK1 receptor in a subject according to claim 1 wherein the compound is represented by the formula (Ib):

[Chem.7]

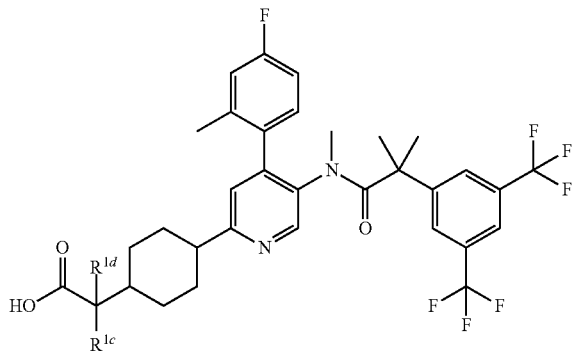

(Ib)

wherein $R^{1c}$ and $R^{1d}$ are each independently a hydrogen atom or methyl;

or a pharmaceutically acceptable salt thereof.

4. A method for the suppression or treatment of a disease mediated by NK1 receptor in a subject, said method comprising administering to said subject a therapeutically effective amount of a compound represented by the following formula:

[Chem.8]

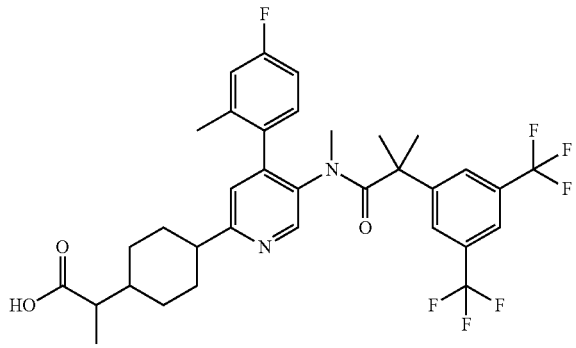

or a pharmaceutically acceptable salt thereof, and wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus pain, migraine, tinnitus, benign prostatic hyperplasia, overactive bladder and urinary incontinence.

5. A method for the suppression or treatment of a disease mediated by NK1 receptor in a subject, said method comprising administering to said subject a therapeutically effective amount of a compound represented by the following formula:

[Chem.9]

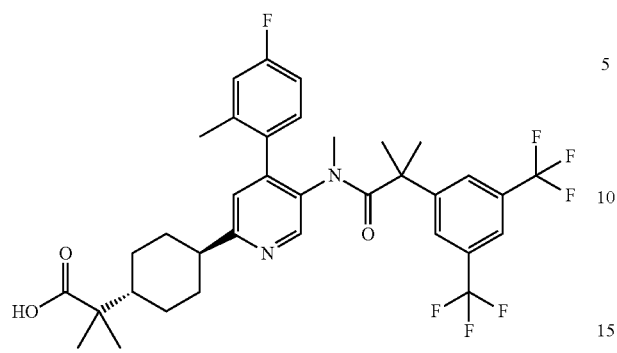

or a pharmaceutically acceptable salt thereof, and
wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia anxiety and depression, alcoholism, irritable bowel syndrome, ulcerative colitis, coughing, asthma, atopic dermatitis, psoriasis, pruritus, pain, migraine, tinnitus, benign prostatic hyperplasia, overactive bladder and urinary incontinence.

6. A method for the suppression or treatment of a disease mediated by NK1 receptor in a subject, said method comprising administering to said subject a therapeutically effective amount of a compound represented by the following formula:

[Chem.10]

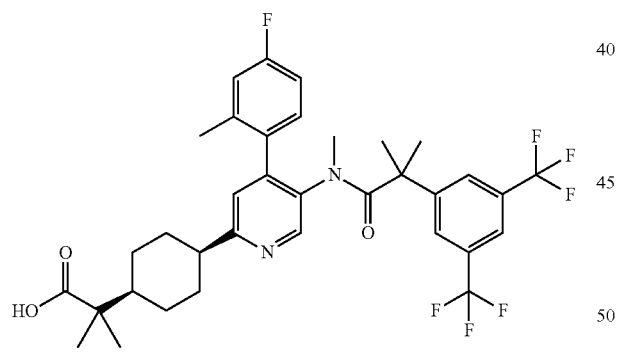

or a pharmaceutically acceptable salt thereof, and
wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus pain, migraine, tinnitus, benign prostatic hyperplasia, overactive bladder and urinary incontinence.

7. A method for the suppression or treatment of a disease mediated by NK1 receptor in a subject, said method comprising administering to said subject a therapeutically effective amount of a compound represented by the following formula:

[Chem.11]

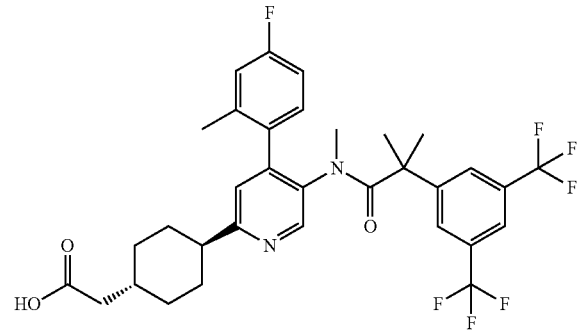 [SMILES: Cc1cc(F)ccc1-c1cc([C@H]2CC[C@H](CC(=O)O)CC2)ncc1N(C)C(=O)C(C)(C)c1cc(C(F)(F)F)cc(C(F)(F)F)c1]

or a pharmaceutically acceptable salt thereof, and
wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus, pain, migraine, tinnitus, benign prostatic hyperplasia, overactive bladder and urinary incontinence.

8. A method for the suppression or treatment of a disease mediated by NK1 receptor in a subject, said method comprising administering to said subject a therapeutically effective amount of a compound represented by the following formula:

[Chem.12]

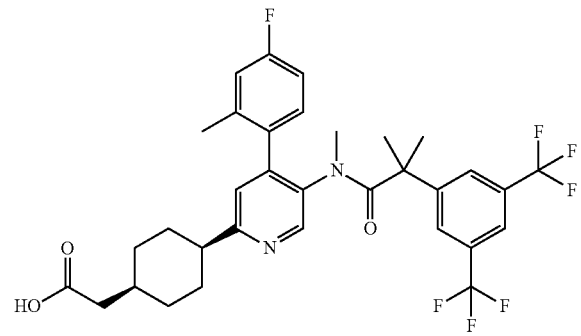 [SMILES: Cc1cc(F)ccc1-c1cc([C@H]2CC[C@@H](CC(=O)O)CC2)ncc1N(C)C(=O)C(C)(C)c1cc(C(F)(F)F)cc(C(F)(F)F)c1]

or a pharmaceutically acceptable salt thereof, and
wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus, pain, migraine, tinnitus, benign prostatic hyperplasia, overactive bladder and urinary incontinence.

9. A method for the suppression or treatment of a disease mediated by NK1 receptor in a subject, said method comprising administering to said subject a therapeutically effective amount of a compound represented by the following formula:

[Chem.13]

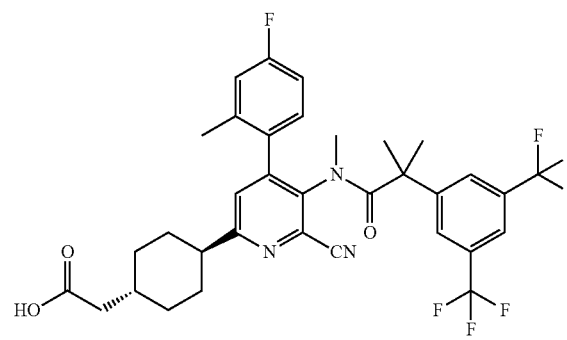

or a pharmaceutically acceptable salt thereof, and
wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus, pain, migraine, tinnitus, benign prostatic hyperplasia overactive bladder and urinary incontinence.

10. A method for the suppression or treatment of a disease mediated by NK1 receptor in a subject, said method comprising administering to said subject a therapeutically effective amount of a compound represented by the following formula:

[Chem.14]

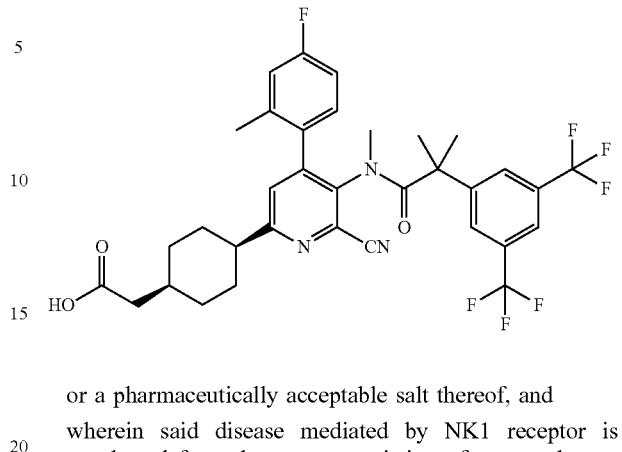

or a pharmaceutically acceptable salt thereof, and
wherein said disease mediated by NK1 receptor is selected from the group consisting of cancer-chemotherapy-induced gastrointestinal symptom, postoperative nausea and vomiting (PONV), nausea and vomiting associated with radiotherapy, morphine-induced vomiting, motion sickness, the treatment of schizophrenia, social phobia, anxiety and depression, alcoholism, irritable bowel syndrome, ulcerative colitis, coughing, asthma, atopic dermatitis, psoriasis, pruritus pain, migraine, tinnitus, benign prostatic hyperplasia, overactive bladder and urinary incontinence.

11. The method of claim 1, wherein said compound is administered orally.

12. The method of claim 1, wherein said compound is administered parenterally.

13. The method of claim 1, wherein said subject is a human.

* * * * *

```
SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: forward primer

<400> SEQUENCE: 1
tacctcgaga gatagtaggg ctttaccg                                        28

<210> SEQ ID NO 2
<211> LENGTH: 28
<212> TYPE: DNA
<213> ORGANISM: Artificial Sequence
<220> FEATURE:
<223> OTHER INFORMATION: reverse primer

<400> SEQUENCE: 2
gccaagcttc taggagagca cattggag                                        28

<210> SEQ ID NO 3
<211> LENGTH: 1224
<212> TYPE: DNA
<213> ORGANISM: Homo sapiens

<400> SEQUENCE: 3
atggataacg tcctcccggt ggactcagac ctctccccaa acatctccac taacacctcg      60
gaacccaatc agttcgtgca accagcctgg caaattgtcc tttgggcagc tgcctacacg     120
gtcattgtgg tgacctctgt ggtgggcaac gtggtagtga tgtggatcat cttagcccac     180
aaaagaatga ggacagtgac gaactatttt ctggtgaacc tggccttcgc ggaggcctcc     240
atggctgcat tcaatacagt ggtgaacttc acctatgctg tccacaacga atggtactac     300
```

```
ggcctgttct actgcaagtt ccacaacttc tttcccatcg ccgctgtctt cgccagtatc    360
tactccatga cggctgtggc ctttgatagg tacatggcca tcatacatcc cctccagccc    420
cggctgtcag ccacagccac caaagtggtc atctgtgtca tctgggtcct ggctctcctg    480
ctggccttcc cccagggcta ctactcaacc acagagacca tgcccagcag agtcgtgtgc    540
atgatcgaat ggccagagca tccgaacaag atttatgaga aagtgtacca catctgtgtg    600
actgtgctga tctacttcct cccctgctg gtgattggct atgcatacac cgtagtggga    660
atcacactat gggccagtga gatccccggg gactcctctg accgctacca cgagcaagtc    720
tctgccaagc gcaaggtggt caaaatgatg attgtcgtgg tgtgcacctt cgccatctgc    780
tggctgccct tccacatctt cttcctcctg ccctacatca acccagatct ctacctgaag    840
aagtttatcc agcaggtcta cctggccatc atgtggctgg ccatgagctc caccatgtac    900
aaccccatca tctactgctg cctcaatgac aggttccgtc tgggcttcaa gcatgccttc    960
cggtgctgcc ccttcatcag cgccggcgac tatgaggggc tggaaatgaa atccacccgg   1020
tatctccaga cccagggcag tgtgtacaaa gtcagccgcc tggagaccac catctccaca   1080
gtggtggggg cccacgagga ggagccagag gacggcccca aggccacacc ctcgtccctg   1140
gacctgacct ccaactgctc ttcacgaagt gactccaaga ccatgacaga gagcttcagc   1200
ttctcctcca atgtgctctc ctag                                         1224
```